US010485797B2

(12) United States Patent
Gourlay

(10) Patent No.: US 10,485,797 B2
(45) Date of Patent: *Nov. 26, 2019

(54) TREATMENT OF PEMPHIGUS

(71) Applicant: Principia Biopharma Inc., South San Francisco, CA (US)

(72) Inventor: Steven Gourlay, San Francisco, CA (US)

(73) Assignee: PRINCIPIA BIOPHARMA INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/537,294

(22) PCT Filed: Dec. 18, 2015

(86) PCT No.: PCT/US2015/066868
§ 371 (c)(1),
(2) Date: Jun. 16, 2017

(87) PCT Pub. No.: WO2016/100914
PCT Pub. Date: Jun. 23, 2016

(65) Prior Publication Data
US 2018/0050027 A1  Feb. 22, 2018

Related U.S. Application Data

(60) Provisional application No. 62/093,891, filed on Dec. 18, 2014.

(51) Int. Cl.
| A61K 31/4545 | (2006.01) |
| A61K 45/06 | (2006.01) |
| A61K 31/4985 | (2006.01) |
| A61K 31/505 | (2006.01) |
| A61K 31/519 | (2006.01) |

(52) U.S. Cl.
CPC ...... *A61K 31/4545* (2013.01); *A61K 31/4985* (2013.01); *A61K 31/505* (2013.01); *A61K 31/519* (2013.01); *A61K 45/06* (2013.01)

(58) Field of Classification Search
CPC .................................. A61K 31/4545
USPC ....................................... 514/258.1
See application file for complete search history.

(56) References Cited

U.S. PATENT DOCUMENTS

| 4,721,710 A | 1/1988 | Bernhart et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,514,711 A | 5/1996 | Kitano et al. |
| 5,792,771 A | 8/1998 | App et al. |
| 6,331,555 B1 | 12/2001 | Hirth et al. |
| 6,410,486 B2 | 6/2002 | Wetterich et al. |
| 6,596,746 B1 | 7/2003 | Das et al. |
| 6,660,744 B1 | 12/2003 | Hirst et al. |
| 7,217,682 B2 | 5/2007 | Mori |
| 7,514,444 B2 | 4/2009 | Honigberg et al. |
| 7,700,648 B2 | 4/2010 | Mori |
| 8,673,925 B1* | 3/2014 | Goldstein ............ A61K 31/519 514/262.1 |
| 8,759,358 B1 | 6/2014 | Goldstein |
| 8,940,744 B2 | 1/2015 | Owens et al. |
| 8,946,241 B2 | 2/2015 | Goldstein |
| 8,957,080 B2 | 2/2015 | Goldstein et al. |
| 8,962,635 B2 | 2/2015 | Goldstein |
| 8,962,831 B2 | 2/2015 | Goldstein |
| 9,090,621 B2 | 7/2015 | Goldstein |
| 9,266,895 B2 | 2/2016 | Owens et al. |
| 9,376,438 B2 | 6/2016 | Goldstein et al. |
| 9,572,811 B2 | 2/2017 | Babler et al. |
| 9,688,676 B2 | 6/2017 | Owens et al. |
| 9,994,576 B2 | 6/2018 | Owens et al. |
| 10,092,569 B2 | 10/2018 | Masjedizadeh et al. |
| 2003/0153752 A1 | 8/2003 | Hirst et al. |
| 2003/0187001 A1 | 10/2003 | Calderwood et al. |
| 2004/0006083 A1 | 1/2004 | Hirst et al. |
| 2004/0157847 A1 | 8/2004 | Field et al. |
| 2005/0008640 A1 | 1/2005 | Waegell et al. |
| 2005/0026945 A1 | 2/2005 | Kafka et al. |
| 2005/0065176 A1 | 3/2005 | Field et al. |
| 2006/0025383 A1 | 2/2006 | Wishart et al. |

(Continued)

FOREIGN PATENT DOCUMENTS

| CN | 101610676 A | 12/2009 |
| CN | 101730699 A | 6/2010 |

(Continued)

OTHER PUBLICATIONS

Robak,Expert opinion on investigational drugs (2012), 21(7), 921-47.*
Grando, Autoimmunity, 2012; 45(1): 7-35.*
Dias, A.L, "Ibrutinib: A New Frontier in the Treatment of Chronic Lymphocytic Leukemia by Bruton's Tyrosine Kinase Inhibition," *Cardiovascular & Hematological Agents in Medicinal Chemistry*, vol. 11, No. 4, pp. 265-271 (2014).
Di Paolo, J.A. et al., "Specific Btk Inhibition Suppresses B Cell- and Myeloid Cell-Mediated Arthritis," *Nat.Chem. Biol.*, vol. 7., pp. 41-50 (2011).
Evans, E.K. et al., "Inhibition of Btk with CC-292 Provides Early Pharmacodynamic Assessment of Activity in Mice and Humans," *J. Pharm. Exp. Ther.*, vol. 346. No. 2, pp. 219-228 (Aug. 2013).

(Continued)

*Primary Examiner* — Nizal S Chandrakumar
(74) *Attorney, Agent, or Firm* — Finnegan, Henderson, Farabow, Garrett & Dunner, LLP

(57) ABSTRACT

The present disclosure provides methods of treating with a BTK inhibitor a blistering disease, in particular pemphigus vulgaris or pemphigus folliaceous in a mammal, use of a BTK inhibitor as a replacement therapy for corticosteroid therapy for diseases treatable with a corticosteroid, such as autoimmune or inflammatory disease and in particular where corticosteroids are used as first or second line therapy, and pharmaceutical formulations comprising the same.

18 Claims, 2 Drawing Sheets

(56) References Cited

U.S. PATENT DOCUMENTS

| | | |
|---|---|---|
| 2006/0058297 A1 | 3/2006 | Roifman et al. |
| 2006/0058324 A1 | 3/2006 | Capraro et al. |
| 2006/0079494 A1 | 4/2006 | Santi et al. |
| 2007/0149464 A1 | 6/2007 | Billen et al. |
| 2007/0149550 A1 | 6/2007 | Billen et al. |
| 2007/0232668 A1 | 10/2007 | Priebe et al. |
| 2007/0232688 A1 | 10/2007 | Orchansky et al. |
| 2008/0076921 A1 | 3/2008 | Honigberg et al. |
| 2008/0146643 A1 | 6/2008 | Billen et al. |
| 2008/0176865 A1 | 7/2008 | Billen et al. |
| 2008/0260818 A1 | 10/2008 | Penhasi et al. |
| 2009/0215750 A1 | 8/2009 | Bamberg et al. |
| 2009/0215788 A1 | 8/2009 | Elworthy et al. |
| 2009/0306396 A1 | 12/2009 | Toyoshima et al. |
| 2010/0113520 A1 | 5/2010 | Miller |
| 2010/0144705 A1 | 6/2010 | Miller |
| 2010/0152143 A1 | 6/2010 | Priebe et al. |
| 2010/0254905 A1 | 10/2010 | Honigberg et al. |
| 2011/0021518 A1 | 1/2011 | Magnuson et al. |
| 2011/0086866 A1 | 4/2011 | Chen et al. |
| 2012/0028981 A1 | 2/2012 | Miller |
| 2012/0071497 A1 | 3/2012 | Buggy et al. |
| 2013/0079327 A1 | 3/2013 | Yamamoto et al. |
| 2013/0197014 A1 | 8/2013 | Chen et al. |
| 2014/0094459 A1 | 4/2014 | Goldstein et al. |
| 2014/0142099 A1 | 5/2014 | Owens |
| 2014/0221398 A1 | 8/2014 | Goldstein et al. |
| 2014/0256734 A1* | 9/2014 | Lawson ............... C07D 403/14 514/249 |
| 2014/0303190 A1 | 10/2014 | Goldstein |
| 2014/0364410 A1 | 12/2014 | Owens et al. |
| 2015/0140085 A1 | 5/2015 | Goldstein |
| 2015/0353557 A1 | 12/2015 | Goldstein et al. |
| 2015/0353562 A1 | 12/2015 | Goldstein |
| 2016/0045503 A1 | 2/2016 | Goldstein et al. |
| 2016/0257686 A1 | 9/2016 | Owens |
| 2016/0376277 A1 | 12/2016 | Desai et al. |
| 2018/0015088 A1 | 1/2018 | Nunn et al. |
| 2018/0050027 A1 | 2/2018 | Gourlay |
| 2018/0162861 A1 | 6/2018 | Goldstein et al. |
| 2018/0193274 A1 | 7/2018 | Nunn et al. |
| 2018/0305350 A1 | 10/2018 | Goldstein et al. |
| 2018/0327413 A1 | 11/2018 | Owens et al. |
| 2019/0076435 A1 | 3/2019 | Masjedizadeh et al. |

FOREIGN PATENT DOCUMENTS

| | | |
|---|---|---|
| CN | 101805341 A | 8/2010 |
| CN | 101880243 A | 11/2010 |
| CN | 102159214 A | 8/2011 |
| CN | 103096716 A | 5/2013 |
| CN | 103534258 A | 1/2014 |
| CN | 104640861 A | 5/2015 |
| CN | 105753863 A | 7/2016 |
| EP | 0461546 A2 | 12/1991 |
| EP | 0493767 A2 | 7/1992 |
| EP | 0908457 A1 | 4/1999 |
| EP | 2443929 A1 | 4/2012 |
| EP | 2578585 A1 | 4/2013 |
| FR | 2535721 A1 | 5/1984 |
| GB | 2447933 A | 10/2008 |
| JP | 56-63950 A | 5/1981 |
| JP | 02-1450 A | 1/1990 |
| JP | 04-177244 A | 6/1992 |
| JP | 2005-239657 A | 9/2005 |
| JP | 2010-504324 A | 2/2010 |
| JP | 2010-235628 A | 10/2010 |
| JP | 2014-513729 A | 6/2014 |
| JP | 2014-517838 A | 7/2014 |
| JP | 6203848 | 9/2017 |
| WO | WO 95/24190 A2 | 9/1995 |
| WO | WO 95/31432 A1 | 11/1995 |
| WO | WO 99/14216 A1 | 3/1999 |
| WO | WO 01/72751 A1 | 10/2001 |
| WO | WO 02/066463 A1 | 8/2002 |
| WO | WO 03/037890 A2 | 5/2003 |
| WO | WO 03/050080 A1 | 6/2003 |
| WO | WO 03/068157 A2 | 8/2003 |
| WO | WO 03/082807 A2 | 10/2003 |
| WO | WO 2004/016259 A1 | 2/2004 |
| WO | WO 2004/074283 A1 | 9/2004 |
| WO | WO 2005/023773 A1 | 3/2005 |
| WO | WO 2005/030184 A2 | 4/2005 |
| WO | WO 2005/085210 A1 | 9/2005 |
| WO | WO 2006/086634 A2 | 8/2006 |
| WO | WO 2006/134468 A1 | 12/2006 |
| WO | WO 2007/043401 A1 | 4/2007 |
| WO | WO 2007/087068 A2 | 8/2007 |
| WO | WO 2007/130075 A1 | 11/2007 |
| WO | WO 2007/142755 A2 | 12/2007 |
| WO | WO 2008/005954 A2 | 1/2008 |
| WO | WO 2008/006032 A1 | 1/2008 |
| WO | WO 2008/039218 A2 | 4/2008 |
| WO | WO 2008/054827 A2 | 5/2008 |
| WO | WO 2008/061740 A1 | 5/2008 |
| WO | WO 2008/072053 A2 | 6/2008 |
| WO | WO 2008/072077 A2 | 6/2008 |
| WO | WO 98/41499 A1 | 9/2008 |
| WO | WO 2008/116064 A2 | 9/2008 |
| WO | WO 2008/121742 A2 | 10/2008 |
| WO | WO 2009/140128 A2 | 11/2009 |
| WO | WO 2009/143477 A1 | 11/2009 |
| WO | WO 2010/009342 A2 | 1/2010 |
| WO | WO 2010/014930 A2 | 2/2010 |
| WO | WO 2010/065898 A2 | 6/2010 |
| WO | WO 2011/031896 A2 | 3/2011 |
| WO | WO 2011/046964 A2 | 4/2011 |
| WO | WO 2011/060440 A2 | 5/2011 |
| WO | WO 2011/144585 A1 | 11/2011 |
| WO | WO 2011/152351 A1 | 12/2011 |
| WO | WO 2011/153514 A2 | 12/2011 |
| WO | WO 2012/021444 A1 | 2/2012 |
| WO | WO 2012/158764 A1 | 11/2012 |
| WO | WO 2012/158795 A1 | 11/2012 |
| WO | WO 2012/158810 A1 | 11/2012 |
| WO | WO 2012/158843 A2 | 11/2012 |
| WO | WO 2013/003629 A2 | 1/2013 |
| WO | WO 2013/010136 A2 | 1/2013 |
| WO | WO 2013/010380 A1 | 1/2013 |
| WO | WO 2013/010869 A1 | 1/2013 |
| WO | WO 2013010868 * | 1/2013 ........... A61K 31/506 |
| WO | WO 2013/041605 A1 | 3/2013 |
| WO | WO 2013/059738 A1 | 4/2013 |
| WO | WO 2013/102059 A1 | 7/2013 |
| WO | WO 2013/116382 A1 | 8/2013 |
| WO | WO 2013/185082 A2 | 12/2013 |
| WO | WO 2013/191965 A1 | 12/2013 |
| WO | WO 2013185082 * | 12/2013 ........... A61K 31/506 |
| WO | WO 2014/004707 A1 | 1/2014 |
| WO | WO 2014/022569 A1 | 2/2014 |
| WO | WO 2014/039899 A1 | 3/2014 |
| WO | WO 2014/068527 A1 | 5/2014 |
| WO | WO 2014/078578 A1 | 5/2014 |
| WO | WO 2014/164558 A1 | 10/2014 |
| WO | WO 2015/127310 A1 | 8/2015 |
| WO | WO 2015/132799 A2 | 9/2015 |
| WO | WO 2017/041536 A1 | 3/2017 |
| WO | WO 2017/066014 A1 | 4/2017 |

OTHER PUBLICATIONS

Honigberg, L.A. et al., "The Bruton Tyrosine Kinase Inhibitor PCI-32765 Blocks B-Cell Activation and Is Efficacious in Models of Autoimmune Disease and B-Cell Malignacy," *Proc Natl Acad Sci*, vol. 107, No. 29, pp. 13075-13080 (2010).

Kanwar, A.J. et al., "Rituximab in Pemphigus," *Indian J. Dermatol. Venereol. Leprol.* [serial online] 2012, 78:671-676, http://www.ijdvl.com/text.asp?2012/78/6/671/102354.

PCT International Search Report and Written Opinion dated Mar. 9, 2016, issued in corresponding International Application No. PCT/US2015/066868, (13 pages).

(56) References Cited

OTHER PUBLICATIONS

Rankin, A.L. et al., "Selective Inhibition of BTK Prevents Murine Lupus and Antibody-Mediated Glomerulonephritis," *J. Immunol.*, vol. 191. No. 9, pp. 4540-4550 (2013).
Xu, D. et al., "RN486, a Selective Bruton's Tyrosine Kinase Inhibitor, Abrogates Immune Hypersensitivity Responses and Arthritis in Rodents," *J. Pharm. Exp. Ther.*, vol. 341. No. 1, pp. 90-103 (2012).
2012 ICD-9-CM Diagnosis Code 372.30: Conjunctivitis, unspecified, retrieved Aug. 4, 2016 (1 page).
Abstract for Neplyuev, V.M. (1979), "Studies of triacylmethanes VII. 1,1,3,3-Tetraacyl-3-arylazo-1-propenes," *Zhumal Organicheskoi Khimii*, 15(3): 563-566 (1 page).
Abstract for Neplyuev, V.M. (1983), "Nitration and nitrosation of 1,1,3,3-tetraacyl-1-propenes" *Ukrainskii Khimicheskii Zhumal* (Russian Edition), 49(2):192-194 (1 page).
Abdulahad, W.H. et al. (2012), "Immune regulation and B-cell depletion therapy in patients with primary Sjögren's syndrome," *J. Autoimmun*, 39(1): 103-111 (2012).
American Cancer Society. Can Non-Hodgkin's Lymphoma Be Prevented? (2016) Web: <https://www.cancer.org/cancer/non-hodgkin-lymphoma/causes-risks—prevention/prevention.html> (3 pages).
Ansel, H.C. et al., "Pharmaceutical Dosage Forms and Drug Delivery Systems," Seventh Edition, Lippincott Williams & Wilkins, A Wolters Kluwer Company, Chapters 1-8, pp. 1-243 (1999).
Armesto, D. et al. (2010), "Efficient photochemical synthesis of 2-vinylcyclopropanecarbaldehydes, precursors of cyclopropane components present in pyrethroids, by using the oxa-di-$\pi$-methane rearrangement," *Tetrahedron*, 66: 8690-8697.
Arnold, L.D. et al. (2000), "Pyrrolo[2,3-d]pyrimidines Containing an Extended 5-Substituent as Potent and Selective Inhibitors of Ick I," *Bioorg. Med. Chem. Lett.*, 10:2167-2170.
Arora, A. & E.M. Scholar (2005), "Role of Tyrosine Kinase Inhibitors in Cancer Therapy," *J. Pharmacol. Exp. Ther.*, 315(3):971-979.
Basheer, A. et al. (2007), "Enols of Substituted Cyanomalonamides," *J. Org. Chem.* 72:5297-5312.
Bastin, R.J. et al. (2000), "Salt Selection and Optimisation Procedures for Pharmaceutical New Chemical Entities," *Org. Process Res. Dev*, 4:427-435.
Berge, S.M. et al. (1977), "Pharmaceutical Salts," *J. Pharm. Sci.*, 66:1-19.
Bernhart, C.A. et al. (1983), "Synthesis and Antiarrhythmic activity of New [(Dialkylamino)alkyl]pyridylacetamides," *J. Med. Chem.*, 26:451-455.
Bradshaw, J. et al. (2015) "Prolonged and tunable residence time using reversible covalent kinase inhibitors," *Nat. Chem. Biol.*, 11:525-531 (with online methods) (10 pages).
Burchat, A.F. et al. (2000), "Pyrrolo[2,3-d]pyrimidines Containing an Extended 5-Substituent as Potent and Selective Inhibitors of Ick II," *Bioorg. Med. Chem. Lett*, 10:2171-2174.
Burini, E. et al. (2005), "Efficient Synthesis of 4-Cyano 2,3-Dihydrooxazoles by Direct Amination of 2-Alkylidene 3-Oxo Nitriles," *Synlett*, 17: 2673-2675.
Calderwood, D.J. et al. (2002), "Pyrrolo[2,3-d]pyrimidines Containing Diverse N-7 Substituents as Potent Inhibitors of Lck," *Bioorg. Med. Chem. Lett.*, 12:1683-1686.
CAS RN 26272-41-3, STN entered Nov. 16, 1984 (1 page).
Certified English Translation of CN 105753863 A, published in Chinese on Jul. 13, 2016 (57 pages).
Cohen, M.S. et al. (2005), "Structural Bioinformatics-Based Design of Selective, Irreversible Kinase Inhibitors," *Science*, 308:1318-1321.
Deng, Y.-R. et al. (2013), "Reversible phospho-Smad3 signalling between tumour suppression and fibrocarcinogenesis in chronic hepatitis B infection," *Clin. Exp. Immunol.*, 176:102-111.
Donald, A. et al. (2007), "Rapid Evolution of 6-Phenylpurine Inhibitors of Protein Kinase B through Structure-Based Design," *J. Med. Chem.*, 50:2289-2292.

Elinson, M.N. et al. (1998), "Electrochemical transformation of cyanoacetic ester and alkylidenecyanoacetic esters into 3-substituted 1,2-dicyanocyclopropane-1,2-dicarboxylates," *Russian Chemical Bulletin*, 47(6):1133-1136.
Elliott, M. et al., "The Pyrethrins and Related Compounds. Part XVIII. Insecticidal 2,2-Dimethylcyclopropanecarboxylates with New Unsaturated 3- Substituents," Journal of the Chemical Society, Perkin Transactions 1: Organic and Bio-Organic Chemistry (1972-1999) (1974), (21), 2470-2474.
Elliott, M. et al. (1976), "Insecticidal activity of the Pyrethrins and Related Compounds X.$^a$ 5-Benzyl-3-furylmethyl 2,2-dimethylcyclopropanecarboxylates with ethylenic substituents at position 3 on the cyclopropane ring," *Pestic. Sci.*, 7: 499-502.
English Language Abstract for JP 42008308 B4, published Apr. 8, 1967, by Yoshitomi Pharmaceutical Industries, Ltd. (1 page).
Fioravanti, S. et al. (2006), "Parallel Solution-Phase Synthesis of Acrylonitrile Scaffolds Carrying $_L$-$\alpha$-Amino Acidic or D-Glycosyl Residues," *J. Comb. Chem.*, 8: 808-811.
Ghoreschi, K. et al. (2009), "Janus kinases in immune cell signaling," *Immunol Rev.*, 228:273-287.
Gyoung, Y.S. et al. (2000), "Regiospecific synthesis of 2-allylated-5-substituted tetrazoles via palladium-catalyzed reaction of nitriles, trimethylsilyl azide, and allyl acetates," *Tetrahedron Lett.*, 41(21): 4193-4196.
Hackam, D.G. & D.A. Redelmeier (2006), "Translation of Research Evidence from Animals to Humans," *JAMA*, 296(14):1731-1732.
Hantschel, O. et al. (2007), "The Btk tyrosine kinase is a major target of the Bcr-Abl inhibitor dasatinib." *PNAS*, 104(33): 13283-13288.
Jenner, G. (2001), "Steric effects in high pressure Knoevenagel reactions," *Tetrahedron Lett.*, 42(2): 243-245.
Johnson, M. & K.J. Corcoran, "Coding for Dry Eye," Optometric Management, Issue: Mar. 2004 (7 pages).
Jordan, V.C. (2003), "Tamoxifen: A Most Unlikely Pioneering Medicine," *Nat. Rev. Drug Discov.*, 2:205-213.
Kamath, S. & Buolamwini J.K. (2003), "Receptor-Guided Alignment-Based Comparative 3D-QSAR Studies of Benzylidene Malonitrile Tyrphostins as EGFR and HER-2 Kinase Inhibitors," *J. Med. Chem.*, 46:4657-4668.
Kamijo, S. et al. (2003), "Tetrazole synthesis via the palladium-catalyzed three component coupling reaction," *Molecular Diversity*, 6:181-192.
Knight, Z.A. et al. (2007), "A membrane capture assay for lipid kinase activity," *Nat. Protoc.*, 2(10):2459-2466.
Kojima, S. et al. (2004), "Stereoselective synthesis of activated cyclopropanes with an $\alpha$-pyridinium acetamide bearing an 8-phenylmenthyl group as the chiral auxiliary," *Tetrahedron Lett.*, 45(18): 3565-3568.
Komura, K. et al. (2007), "Layered silicate PLS-1: A new solid base catalyst for C—C bond forming reactions," *Catal Commun.*, 8(4): 644-648.
Kotz, A. & W. Zorning, "The Action of Chloroform on Methylene and Methenyl Groups," *Journal fuer Praktische Chemie (Leipzig)*, Abstract, 74: 425-48 (1907).
Leopold, C.S., "A Practical Approach in the Design of Colon-specific Drug Delivery System," Wiley-VCH; Drug Targeting Organ-Specific Strategies, Chapter 6, pp. 157-170 (2001).
Li Zhensu, Medicinal Chemistry, Chemical Industry Press, China, Mar. 3, 1981, pp. 435-436 (2 pages).
Lou, Y. et al. (2012), "Bruton's Tyrosine Kinase Inhibitors: Approaches to Potent and Selective Inhibition, Preclinical and Clinical Evaluation for Inflammatory Diseases and B Cell Malignancies," *J. Med. Chem.*, 55(10): 4539-4550.
Maas, S. et al. (1999), "Conjugate Addition of Dialkylaluminum Chlorides to Alkylidenemalonic Acid Derivatives," *Synthesis*, 10: 1792-1798.
Maurya, R.A. et al. (2013), "Catalyst-free stereoselective cyclopropanation of electron deficient alkenes with ethyl diazoacetate," *RSC Adv.*, 3:15600-15603.
MedicineNet.com. Definition of Cancer. (2004) Web: <http://www.medterms.com> (1 page).
MedlinePlus. Autoimmune Diseases (2014) Web: <https://www.nlm.nih.gov/medlineplus/autoimmunediseases.html> (5 pages).

(56) References Cited

OTHER PUBLICATIONS

Meydan, N. et al. (1996), "Inhibition of acute lymphoblastic leukaemia by a Jak-2 inhibitor," *Nature*, 379:645-648.
Miller, R.M., "Electrophilic Fragment-Based Design of Reversible Covalent Kinase Inhibitors," *J. Am. Chem. Soc.*, 135(14):5298-5301.
Nakamura, M. et al. (2012), "Diquafosol Ophthalmic Solution for Dry Eye Treatment," *Adv Ther*, 29(7):579-589.
Pan, Z. et al. (2007), "Discovery of Selective Irreversible Inhibitors for Bruton's Tyrosine Kinase," *ChemMedChem*, 2:58-61.
Patani, G. & E. Lavoie (1996), "Bioisosterism: A Rational Approach in Drug Design," *Chem. Rev.*, 96:3147-3176.
Pennington, L.D. et al., "The Necessary Nitrogen Atom: A Versatile High-Impact Design Element for Multiparameter Optimization," *J. Med. Chem.*, ePub Feb. 8, 2017, 28 pages, DOI: 10.1021/acs.jmedchem.6b01807.
Porter, D.W. et al. (2014), "The discovery of potent, orally bioavailable pyrimidine-5-carbonitrile-6-alkyl CXCR2 receptor antagonists," *Bioorg. Med. Chem. Lett.*, 24: 3285-3290.
Proenca, F. & Costa, M. (2008), "A simple and eco-friendly approach for the synthesis of 2-imino and 2-oxo-2H-chromene-3-carboxamides,"*Green Chem.*, 10:995-998.
Rellos, P. et al. (2007), "Structure and Regulation of the Human Nek2 Centrosomal Kinase," *J. Biol. Chem.*, 282(9):6833-6842.
Sammes, M.P., et al. (1971), "α-Cyano-sulphonyl Chlorides: Their Preparation and Reactions with Amines, Alcohols, and Enamines," *J. Chem. Soc.*, 1:2151-2155.
Santilli, A.A. & T.S. Osdene (1964), "8,9,10,11-Tetrahydro-12H-benzo[5,6]quinoxalino[2,3-e][1,4]diazepin-12-ones. Examples of a New Heterocyclic Ring System," *J. Org. Chem.*, 29:2066-2068.
Santus, G. & R.W. Baker (1995), "Osmotic Drug Delivery: A Review of the Patent Literature," *J. Control. Release*, 35:1-21.
Schwarz, J.B. et al. (2005), "Novel Cyclopropyl β-Amino Acid Analogues of Pregabalin and Gabapentin That Target the $\alpha_2$-δProtein," *J. Med. Chem.*, 48:3026-3035.
Schwöbel, J. et al. (2010), "Prediction of Michael-Type Acceptor Reactivity toward Glutathione," *Chem. Res. Toxicol.*, 23, 1576-1585.
Serafimova, I.M. et al. (2012), "Reversible targeting of noncatalytic cysteines with chemically tuned electrophiles," *Nat. Chem. Biol.*, ePub Apr. 1, 2012, 6 pages, DOI: 10.1038/nchembio.925.
Stahl, P. Heirich & C.G. Wermuth (Eds.) (2002), Handbook of Pharmaceutical Salts: Properties, Selection, and Use, Wiley-VCH; pp. 1-374.
Stevens, C.V. et al. (2002), "Synthesis of Substituted Cyclopropylphosphonates by Michael Induced Ring Closure (MIRC) Reactions," *Synlett*, 7:1089-1092.
Structure-Based Search Results (May 9, 2011, 8:13 PM), SciFinder (2 pages).
Structure-Based Search Results (May 9, 2011, 8:23 PM), SciFinder (2 pages).
Structure-Based Search Results (May 9, 2011, 8:33 PM), SciFinder (2 pages).
Structure-Based Search Results (May 9, 2011, 9:06 PM), SciFinder (2 pages).
Structure-Based Search Results (May 10, 2011, 10:04 AM), SciFinder (6 pages).
Structure-Based Search Results (May 10, 2011, 10:20 AM), SciFinder (4 pages).
Structure-Based Search Results (May 10, 2011, 10:46 AM), SciFinder (4 pages).
Verhé, R. et al. (1978), "Preparation of 2,2-Dialkylcyclopropanes Geminally Substituted with Electron-Withdrawing Groups," *Synthesis*, 7:530-532.
Verhé, R. et al. (1978), "Thermal Lactonization of Brominated Alkylidenemalonates: Synthesis Of 2-Buten-4-Olides," *Bulletin des Societes Chimiques Belges*, 87(3):215-222.
Verhé, R. et al. (1981), "Synthesis of 1,1-Bis(Hydroxymethyl) Cyclopropanes," *Org. Prep. Proced. Int.*, 13(1):13-18.
Vo, N. H. et al. (1997), "Transformations of Resin-Bound Pyridinium Ylides: I. A Stereoselective Synthesis of 2,2,3-Trisubstituted Cyclopropanecarboxylates," *Tetrahedron Lett.*, 38(46):7951-7954.
Wang, K. et al. (2009), "'Cyanoacetamide Multicomponent Reaction (I): Parallel Synthesis of Cyanoacetamides," *J. Comb. Chem.*, 11:920-927.
Wang, G.T. et al. (2010), "Substituted 4-amino-1H-pyrazolo[3,4-d]pyrimidines as multi-targeted inhibitors of insulin-like growth factor-I receptor (IGFIR) and members of ErbB-family receptor kinases," *Bioorg. Med. Chem. Lett.*, 20:6067-6071.
WebMD. 10 Ways to Prevent Psoriasis Flare-Ups. (2016) Web: <http://www.webmd.com/skin-problems-and-treatments/psoriasis/prevent-flare-ups> (8 pages).
WebMD. Multiple Sclerosis (MS)-Prevention. (2015) Web: < http://www.webmd.com/multiple-sclerosis/tc/multiple-sclerosis-ms-prevention> (4 pages).
Wells, G. et al. (2000), "Structural Studies on Bioactive Compounds. 32.[1] Oxidation of Tyrphostin Protein Tyrosine Kinase Inhibitors with Hypervalent Iodine Reagents," *J. Med. Chem.*, 43:1550-1562.
WhatisDryEye.com. Dry Eye vs. Conjunctivitis (2016) Web: <http://www.whatisdryeye.com/dry-eye-vs-conjunctivitis> (5 pages).
Wilding, I.R. et al. (1994), "Targeting of Drugs and Vaccines to the Gut," *Pharmac. Ther.*, 62:97-124.
Wissner, A. et al. (2003), "Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)," *J. Med. Chem.*, 46:49-63.
Zhang, F. et al. (2009), "Organic base catalyzed carbonyl allylation of methyl trifluoropyruvate with activated alkenes," *Tetrahedron*, 65:83-86.
Zimmerman, H.E. & W. Chen (2002), "The Diverted Di-π-Methane Rearrangement; Mechanistic and Exploratory Organic Photochemistry," *Org. Lett.*, 4(7): 1155-1158.
Communication Pursuant to Article 94(3) EPC for European Patent Application No. 13731218.7, dated Sep. 23, 2015 (4 pages).
English Translation of Office Action dated Apr. 12, 2013, in Chinese Application No. 201080061570.1 (2 pages).
Extended European Search Report for European Patent Application No. 17152898.7, dated Mar. 8, 2017 (7 pages).
International Preliminary Report on Patentability, dated May 22, 2012, in International Application No. PCT/US2010/056890, filed Nov. 16, 2010, by the Regents of the University of California (10 pages).
International Search Report dated Jul. 28, 2011, in International Application No. PCT/US2010/056890, filed Nov. 16, 2010, by the Regents of the University of California (7 pages).
International Search Report and Written Opinion dated Jul. 5, 2012, in International Patent Application No. PCT/US2012/038092, filed May 16, 2012, by Principia Biopharma Inc. (8 pages).
International Search Report and Written Opinion dated Aug. 20, 2012, in International Patent Application No. PCT/US2012/038120, filed May 16, 2012, by Principia Biopharma Inc. (10 pages).
International Search Report and Written Opinion dated Jul. 25, 2012, in International Application No. PCT/US2012/038135, filed May 16, 2012, by Principia Biopharma Inc. (9 pages).
International Search Report and Written Opinion dated Jul. 9, 2012, in International Patent Application No. PCT/US2012/038163, filed May 16, 2012, by Principia Biopharma Inc. (8 pages).
International Search Report dated Feb. 1, 2013, for International Application No. PCT/US2012/038214, filed May 16, 2012, by the Regents of the University of California et al. (5 pages).
International Search Report and Written Opinion dated Sep. 3, 2013, in International Patent Application No. PCT/US2013/045266, filed Jun. 11, 2013, by Principia Biopharma Inc. (11 pages).
International Search Report and Written Opinion dated Oct. 1, 2013, in International Patent Application No. PCT/US2013/047958, filed Jun. 26, 2013, by Principia Biopharma Inc. (14 pages).
International Search Report and Written Opinion dated Nov. 18, 2013, in International Patent Application No. PCT/US2013/053042, filed Jul. 31, 2013, by Principia Biopharma Inc. (12 pages).

(56) References Cited

OTHER PUBLICATIONS

International Search Report and Written Opinion dated Nov. 5, 2013, in International Patent Application No. PCT/US2013/058614, filed Sep. 6, 2013, by Principia Biopharma Inc. (11 pages).
International Search Report and Written Opinion dated Apr. 22, 2015, in International Patent Application No. PCT/US2015/016963, filed Feb. 20, 2015, by Mohammad Reza Masjedizadeh et al. (10 pages).
International Search Report and Written Opinion dated Apr. 18, 2016, in International Patent Application No. PCT/US2015/000515, filed Dec. 23, 2015, by Philip A. Nunn et al. (11 pages).
International Search Report and Written Opinion dated Mar. 21, 2016, in International Patent Application No. PCT/US2015/000303, filed Dec. 23, 2015, by Philip Nunn et al. (12 pages).
International Search Report and Written Opinion dated Aug. 16, 2016, in International Patent Application No. PCT/US2016/035588, filed Jun. 2, 2016, by Principia Biopharma Inc. (10 pages).
International Search Report and Written Opinion dated Oct. 6, 2016, in International Patent Application No. PCT/US2016/039070, filed Jun. 23, 2016, by Principia Biopharma Inc. (18 pages).
International Search Report and Written Opinion dated Oct. 2, 2017, in International Patent Application No. PCT/US2017/040075, filed Jun. 29, 2017, by Principia Biopharma Inc. (9 pages).
U.S. Appl. No. 15/072,244, filed Mar. 16, 2016, by Principia Biopharma Inc.
U.S. Appl. No. 15/188,941, filed Jun. 21, 2016, by Principia Biopharma Inc.
U.S. Appl. No. 16/312,258, filed Dec. 20, 2018, by Principia Biopharma Inc.

\* cited by examiner

FIG. 1A. Pretreatment.
FIG. 1B. Nose fully cleared 28 days after treatment.

FIG. 2A. Pretreatment.
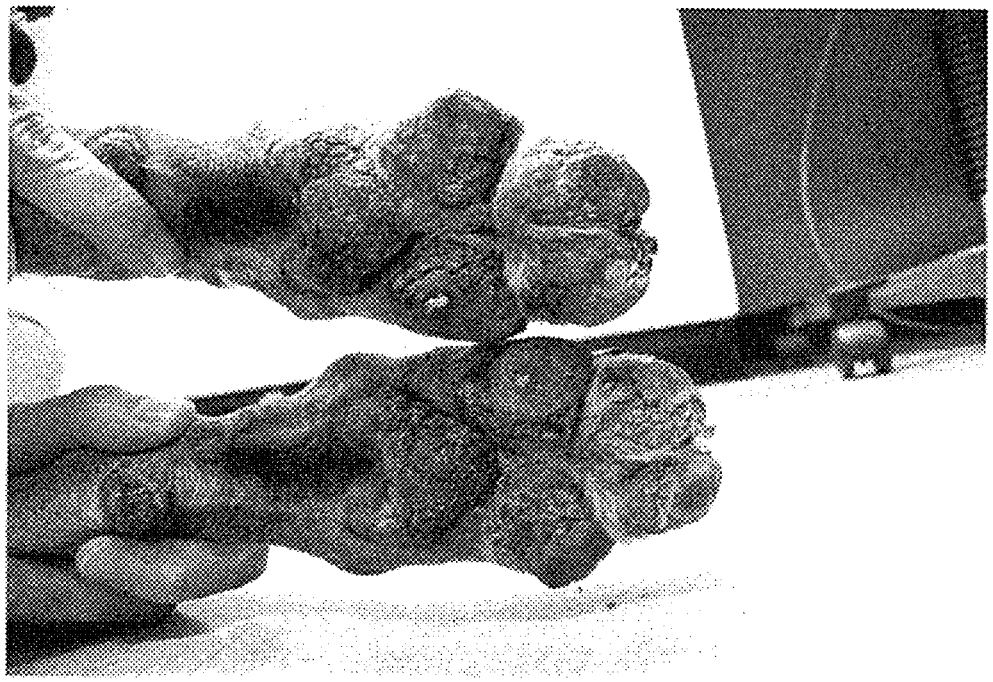
FIG. 2B. Full healing after 28 days treatment: feet pad normal (normal gait resumed within a few days).
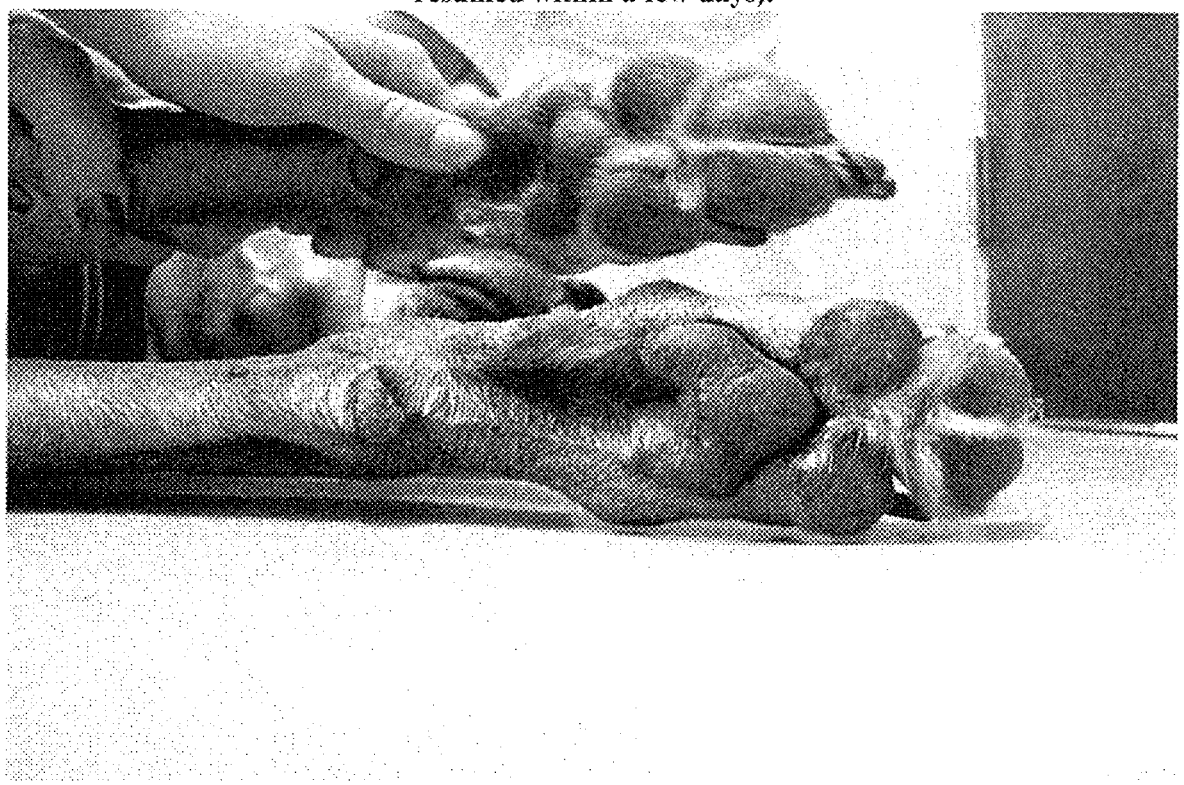

TREATMENT OF PEMPHIGUS

This application is a national phase application based on international application number PCT/US2015/066868, filed Dec. 18, 2015, which claims the benefit of priority to U.S. provisional patent application Ser. No. 62/093,891, filed Dec. 18, 2014, the contents of each of which are incorporated by reference herein.

This application claims the benefit of priority to U.S. provisional patent application Ser. No. 62/093,891, filed Dec. 18, 2014; the contents of which are incorporated by reference herein.

The present disclosure provides methods of treating a blistering disease, in particular pemphigus vulgaris or pemphigus foliaceous with a BTK inhibitor in a mammal, use of a BTK inhibitor as a replacement therapy for corticosteroid therapy for diseases treatable with a corticosteroid, such as autoimmune or inflammatory disease and in particular where corticosteroids are used as first or second line therapy, and pharmaceutical formulations comprising the same.

Pemphigus vulgaris (PV) is a tissue-specific autoimmune blistering disease of the skin and mucous membranes in humans (Scully C, Challacombe S. J. Pemphigus vulgaris: update on etiopathogenesis, oral manifestations, and management. Crit Rev Oral Biol Med 2002; 13: 397-408) and is associated with considerable risks of morbidity and mortality. PV patients exhibit severe mucosal erosions and epidermal blistering that rupture easily, leading to erosions and crusts.

The disease is characterized by deposition of immunoglobulin G (IgG) and blister formation just above the basal cell layer of the epidermis. PV is associated with and thought to be driven by autoantibodies against the adhesion molecules desmoglein 3 (Dsg3) and desmoglein 1 (Dsg1), transmembrane proteins belonging to the cadherin family. Dsg3 and Dsg1 play a role connecting cells in the stratified squamous epithelium. Antibodies against Dsg3 and Dsg1 as well as PV patient sera have been associated with disruption of desmosomal function and keratinocyte adhesion (Ugajin T, Yahara H, Moriyama Y, et al. Two siblings with neonatal pemphigus vulgaris associated with mild maternal disease. Br J Dermatol 2007; 157 (1): 192-4). Anti-Dsg3 titres are correlated with the disease activity, and reactivity to certain epitopes on Dsg3 are correlated with clinical phenotype or severity (Campo-Voegeli A. Neonatal pemphigus vulgaris with extensive mucocutaneous lesions from a mother with oral pemphigus vulgaris. Br J Dermatol 2002; 147: 801-5).

At present the mainstay treatment for PV includes high doses of oral or parenteral corticosteroids either alone or in combination with immunosuppressive drugs such as cyclophosphamide, mycophenolate mofetil, methotrexate, dapsone, sulfasalazine or azathioprine (Murrell D F, Autoimmune blistering diseases: Part II—diagnosis and management. Dermatol Clinics Vol 29, No 4, October 2011, Ribeiro A M, Alvarez R R, Friedman H, et al. The profile of fogo selvagem (endemic pemphigus foliaceus) at the University Hospital of Brasilia-Brazil: epidemiological and clinical considerations. Int J Dermatol 2005 April; 44 (4): 293-8). Optimization of these therapies is difficult and significant side effects of corticosteroids, such as weight gain with Cushingoid features, hypertension, disturbances of glucose and calcium metabolism, myopathy, mood disorder, and sepsis, are experienced by patients and contribute to the relatively high mortality in the first year of approximately 5% (Murrell D. F, AutoImmune Blistering Disease Part I, An Issue of Dermatologic Clinics, 1st Edition, ISBN 9781455710331).

Due to severe side effects associated with use of corticosteroid, alternative therapies to corticosteroids for the treatment in PV have been explored and some of them include use of (i) high dose intravenous immunoglobulin (IVIG) administration when conventional immunosuppressive therapies are not effective and (ii) anti-CD20 antibody rituximab, which is approved for treatment of B cell malignancies and is increasing being used to treat autoimmune diseases (Esmaili N, Chams-Davatchi C, Valikhani M, et al. Pemphigus vulgaris in Iran: a clinical study of 140 cases. Int J Dermatol 2007; 46: 1166-70; Mahoney M, Wang Z, Rothenberger K, et al. Explanations for the clinical and microscopic localization of lesions in pemphigus foliaceus and vulgaris. J Clin Invest 1999; 103: 461-8).

The drawbacks of the above therapies is that the IVIG therapy is expensive and has adverse effects such as headache, backache, flushing, fever, nausea and vomiting, anaphylaxis, aseptic meningitis, renal failure, and hypertension (see Product Label) and rituximab has significant delay in clinical response (maximal effect at 8-12 weeks see Lundardon L & Payne A S G Ital Dermatol Venereol 2012; 147(3):269-276) requiring continued corticosteroid therapy for some months and furthermore the durability of the response as measured by anti-keritinocyte antibodies are varied ranging between no relapse to multiple relapses. In addition, patients treated with rituximab suffered serious side effects such as pneumonia (see Morrison L. H. Therapy of refractory pemphigus vulgaris with monoclonal anti-CD20 antibody (rituximab) J Am Acad Dermatol 2004; 51:817-819 and Dupuy A, et. al. Treatment of refractory pemphigus vulgaris with rituximab (anti-CD20 monoclonal antibody) Arch Dermatol. 2004; 140:91-96), neutropenia (see Rios-Fernandez R. et al. Late-onset neutropenia following rituximab treatment in patients with autoimmune disease Br J. Detmatol. 2007; 157:1271-1273 and Goh M. S et al. Rituximab in the adjuvant treatment of pemphigus vulgaris: a prospective open-label pilot study in five patients. Br J. Dermatol. 2007; 156: 990-996), DVT and pulmonary embolism (Shimanovich I. et. al. Treatment of severe pemphigus with protein A immunoadsorption, rituximab and intravenous immunoglobulins Br J. Dermatol 2008; 158:382-388) including death from septic shock (Tournadre A, et al. Polymyositis and pemphigus vulgaris in a patient successful treatment with rituximab Jt Bone Spine 2008; 75:728-729). Accordingly, there is a need for new therapies that can treat PV effectively and related diseases without causing or at least reducing serious side effects compared to the standard of care in treating pemphigus.

In a recent study conducted by the Applicant in which a dog suffering from pemphigus foliaceus (PF) was administered (R,E)-2-(3-(4-amino-3-(2-fluoro-4-phenoxy-phenyl)-1H-pyrazolo[3,4-d]pyrimidin-1-yl)piperidine-1-carbonyl)-4,4-dimethylpent-2-enenitrile, a Bruton Tyrosine Kinase (BTK) inhibitor, as a single agent, it was surprisingly discovered that inhibition of BTK is effective and safe for the treatment of PF.

In addition, it was surprisingly discovered that the manifestation of clinical response with (R,E)-2-(3-(4-amino-3-(2-fluoro-4-phenoxyphenyl)-1H-pyrazolo[3,4-d]-pyrimidin-1-yl)piperidine-1-carbonyl)-4,4-dimethylpent-2-enenitrile, was as rapid and comparable to that observed with systemic corticosteroid therapy. Additionally, none of the well-known corticosteroid-like adverse effects in canines, such as polyuria, polydipsia, polyphagia or weight gain, was observed.

Accordingly, the present disclosure provides methods of treating a blistering disease, such as pemphigus vulgaris (PV) or pemphigus foliaceous (PF) with a BTK inhibitor in a mammal, use of a BTK inhibitor as a replacement therapy for corticosteroid therapy for diseases treatable with a corticosteroid (such as autoimmune or inflammatory disease and in particular where corticosteroids are used as first or second line therapy), where a rapid clinical response is desirable. Also, disclosed are methods of treating autoimmune and/or inflammatory diseases with a BTK inhibitor at a specific phase of the disease process (such as acute phase and/or at onset and duration of an acute flare) and for a limited amount of time so as to maximize short term relief, minimize long term progression of the disease, and minimize long term toxicological and other adverse effects.

FIG. 1A shows the nose of a 30 kg Doberman dog with a characteristic first presentation of pemphigus foliaceous on the nose and paws prior to treatment with a BTK inhibitor. FIG. 1B depicts the same dog's nose twenty-eight days after treatment.

FIG. 2A shows the feet pads of a 30 kg Doberman dog with a characteristic first presentation of pemphigus foliaceous on the nose and paws prior to treatment with a BTK inhibitor. FIG. 2B depicts the same dog's feet pads twenty-eight days after treatment.

Accordingly, in a first aspect, provided is a method of treating an autoimmune blistering disease in a mammal in need thereof which method comprises administering to the mammal in need of said treatment a therapeutically effective amount of a BTK inhibitor.

In a second aspect, provided is a method of treating an acute inflammatory and/or autoimmune disease in a mammal in need thereof where corticosteroid therapy is used as the first or second line therapy comprising administering to said mammal in need of said treatment a therapeutically effective amount of a BTK inhibitor in place of or in combination with said corticosteroid therapy; and optionally administering said BTK inhibitor in combination with a noncorticosteroidal immunosupressive and/or antiinflammatory agents.

In a third aspect, provided is a method of treating an inflammatory and/or autoimmune disease in a mammal in need thereof where corticosteroid therapy is used as the first or second line maintenance therapy comprising administering to said mammal in need of said treatment a therapeutically effective amount of a BTK inhibitor in place of or in combination with said corticosteroid therapy; and optionally administering said BTK inhibitor in combination with a noncorticosteroidal immunosupressive and/or antiinflammatory agent.

In a fourth aspect, provided is a method of eliminating or reducing a therapeutic dose of corticosteroid used in chronic maintenance therapy of an inflammatory and/or autoimmune disease in a mammal in need thereof where corticosteroid therapy is used as the first or second line comprising administering to said mammal in need of said treatment a therapeutically effective amount of a BTK inhibitor in place of or in combination with said corticosteroid chronic maintenance therapy; and optionally administering said BTK inhibitor in combination with a noncorticosteroidal, immunosupressive, and/or antiinflammatory agents.

In a fifth aspect, provided is a method of treating acute flares of an autoimmune and/or inflammatory disease in a mammal in need thereof which method comprises administering to the mammal in need of said treatment a therapeutically effective amount of a BTK inhibitor for a treatment period sufficient to treat acute flares of the autoimmune disease. In one embodiment of the fifth aspect, the BTK inhibitor is used instead of corticosteroid therapy where corticosteroid therapy is normally used as the first or second line to treat flares.

In a first embodiment of the second and fifth aspects, the autoimmune and/or inflammatory disease is chosen from Table (I):

TABLE (I)

| Acute indications for corticosteroid therapy | Effects of B cell therapy if known |
| --- | --- |
| Initial presentations or flares of rheumatic disorders such as psoriatic arthritis, rheumatoid arthritis, ankylosing spondylitis, bursitis, tenosynovitis, gout, synovitis of osteoarthritis, epicondylitis | Rituximab takes 4-12 weeks to take effect in rheumatoid arthritis (ref Rituxan US label) |
| Initial presentation or flares of collagen disease such as systemic lupus erythematosus (SLE), dermato/polymyositis, rheumatic carditis, vasculitis | Rituximab has delayed effect in ANCA-associated vasculitis and achieves remission in only 64% of cases despite concomitant use of corticosteroids for 5 months (Stone et al. 2010). Belimumab, an anti-Blys antibody, has a modest and delayed effect on improvement of chronic SLE including the ability to reduce corticosteroid use to <7.5 mg of prednisone at week 40-52 in no more than 21% of patients (Benlysta US Product Information). |
| Initial presentations or flares of dermatologic diseases such as pemphigus, Stevens-Johnson syndrome, exfoliative dermatitis, mycosis fungoides, severe psoriasis, severe seborrheic dermatitis | Rituximab has delayed effect in pemphigus vulgaris with maximal effect at 8-12 weeks (Lundardon & Payne 2012) |
| Control of incapacitating allergic reactions including asthma, contact or atopic dermatitis, serum sickness, drug hypersensitivity | |
| Initial presentations or flares of ophthalmic diseases including allergic corneal ulcers, | |

TABLE (I)-continued

| Acute indications for corticosteroid therapy | Effects of B cell therapy if known |
|---|---|
| herpes zoster of the eye, anterior or posterior inflammation/uveitis or choroiditis, sympathetic ophthalmia, allergic conjunctivitis, keratitis, chorioretinitis, optic neuritis, iritis, iridocyclitis | |
| Initial presentations or flares of respiratory diseases including symptomatic sarcoidosis, Loeffler's syndrome, berylliosis, fulminating or disseminated tuberculosis, aspiration pneumonitis | |
| Initial presentations or flares of hematologic disorders including idiopathic thrombocytopenic purpura, secondary thrombocytopenia, autoimmune hemolytic anemia, erythroblastopenia, congenital hypoplastic anemia | |
| Acute nephrotic syndrome of SLE | |
| Initial presentations or flares of gastrointestinal disease such as ulcerative colitis, Crohn's disease | |
| Acute neurological trauma to reduce swelling | |

In a second embodiment of the first, second, third, fourth, and fifth aspects, the autoimmune and/or inflammatory disease is chosen from Table (II) below:

TABLE (II)

Indications for Prednisone tablets

Endocrine disorders:

Primary or secondary adrenocortical insufficiency (hydrocortisone or cortisone is the first choice: synthetic analogs may be used in conjunction with mineralocorticoids where applicable; in infancy mineralocorticoid supplementation is of particular importance).
Congenital adrenal hyperplasia
Nonsuppurative thyroiditis
Hypercalcemia associated with cancer
Rheumatic disorders:

As adjunctive therapy for short-term administration (to tide the patient over an acute episode or exacerbation) in:
Psoriatic arthritis
Rheumatoid arthritis, including juvenile rheumatoid arthritis (selected cases may require low-dose maintenance therapy)
Ankylosing spondylitis
Acute and subacute bursitis
Acute nonspecific tenosynovitis
Acute gouty arthritis
Post-traumatic osteoarthritis
Synovitis of osteoarthritis
Epicondylitis
Collagen diseases:

During an exacerbation or as maintenance therapy in selected cases of:
Systemic lupus erythematosus
Systemic dermatomyositis (polymyositis)
Acute rheumatic carditis
Dermatologic diseases:

Pemphigus
Bullous dermatitis herpetiformis
Severe erythema multiforme (Stevens-Johnson syndrome)
Exfoliative dermatitis
Mycosis fungoides
Severe psoriasis
Severe seborrheic dermatitis
Allergic states:

Control of severe or incapacitating allergic conditions intractable to adequate trials of conventional treatment:
Seasonal or perennial allergic rhinitis
Serum sickness

TABLE (II)-continued

Indications for Prednisone tablets

Bronchial asthma
Contact dermatitis
Atopic dermatitis
Drug hypersensitivity reactions
Ophthalmic diseases:

Severe acute and chronic allergic and inflammatory processes involving the eye and its adnexa, such as:
Allergic conjunctivitis
Keratitis
Allergic corneal marginal ulcers
Herpes zoster ophthalmicus
Iritis and iridocyclitis
Chorioretinitis
Anterior segment inflammation
Diffuse posterior uveitis and choroiditis
Optic neuritis
Sympathetic ophthalmia
Respiratory diseases:

Symptomatic sarcoidosis
Loeffler's syndrome not manageable by other means
Berylliosis
Fulminating or disseminated pulmonary tuberculosis when used concurrently with appropriate antituberculous chemotherapy.
Aspiration pneumonitis
Hematologic disorders:

Idiopathic thrombocytopenic purpura in adults
Secondary thrombocytopenia in adults
Acquired (autoimmune) hemolytic anemia
Eythroblastopenia (RBC anemia)
Congenital (erythroid) hypoplastic anemia
Neoplastic diseases:

For palliative management of:
Leukemias and lymphomas in adults
Acute leukemia of childhood
Edematous states:

To induce a diuresis or remission of proteinuria in the nephrotic syndrome, without uremia, of the idiopathic type or that due to lupus erythematosus.
Gastrointestinal diseases:

To tide the patient over a critical period of the disease in:
Ulcerative colitis
Regional enteritis

TABLE (II)-continued

Indications for Prednisone tablets

Nervous system:

Acute exacerbations of multiple sclerosis
Miscellaneous:

Tuberculous meningitis with subarachnoid block or impending block when used concurrently with appropriate antituberculous chemotherapy.
Trichinosis with neurologic or myocardial involvement.

In a third embodiment of the first, second, third, fourth, and fifth aspects, the disease is pemphigus vulgaris (PG) or pemphigus foliaceus (PF). In a fourth embodiment of the first, second, third, fourth, and fifth aspects, and the first and second embodiments contained therein, the BTK inhibitor is administered as a monotherapy. In a fifth embodiment of the first, second, third, fourth, and fifth aspects, and the first, second and third embodiments contained therein, the BTK inhibitor is administered in acute PG or acute PF in place of or in combination with cortisterods and optionally in combination with an immunosuppressive agent chosen from interferon alpha, interferon gamma, cyclophosphamide, tacrolimus, mycophenolate mofetil, methotrexate, dapsone, sulfasalazine, azathioprine, an anti-CD20 agent (such as rituximab, ofatumumab, obinutuzumab, or veltuzumab, or a biosimilar version thereof), anti-TNFalpha agent (such as entanercept, infliximab, golilumab, adalimumab, or certolizumab pegol or a biosimilar version thereof), anti-IL6 agent toward ligand or its receptors (such as tocilizumab, sarilumab, olokizumab, elsililumab, or siltuximab), anti-IL17 agent to ligand or its receptors (such as secukinumab, ustekinumab, brodalumab, or ixekizumab), anti-IL1 agent to ligand or its receptors (such as with rilonacept, canakinumab, or anakinra), anti-IL2 agent to ligand or its receptors (such as basiliximab or daclizumab), anti-CD2 agent such as alefacept, anti-CD3 agent such as muromonab-cd3, anti-CD80/86 agent such as abatacept or belatacept, anti-sphingosine-1-phosphate receptor agent such as fingolimod, anti-CS agent such as eculizumab, anti-integrin alpha4 agent such as natalizumab, anti-$\alpha_4\beta_7$ agent such as vedolizumab, anti-mTOR agent such as sirolimus or everolimus, anti-calcineurin agent such as tacrolimus, or anti-BAFF/BlyS agent (such as belimumab, VAY736, or blisibimod), leflunomide and teriflunomide. Preferably, rituximab, ofatumumab, obinutuzumab, or veltuzumab, or a biosimilar version thereof.

In a sixth embodiment of the first, second, third, fourth, and fifth aspects, and the first second, and third embodiments contained therein, the BTK inhibitor is administered in acute pemphigus vulgaris or acute pemphigus foliaceus in place of corticosteroids and optionally in combinations with an immunosuppressive agent chosen from interferon alpha, interferon gamma, cyclophosphamide, tacrolimus, mycophenolate mofetil, methotrexate, dapsone, sulfasalazine, azathioprine, an anti-CD20 agent (such as rituximab, ofatumumab, obinutuzumab, or veltuzumab, or a biosimilar version thereof), anti-TNFalpha agent (such as entanercept, infliximab, golilumab, adalimumab, or certolizumab pegol or a biosimilar version thereof), anti-IL6 agent toward ligand or its receptors (such as tocilizumab, sarilumab, olokizumab, elsililumab, or siltuximab), anti-IL17 agent to ligand or its receptors (such as secukinumab, ustekinumab, brodalumab, or ixekizumab), anti-IL1 agent to ligand or its receptors (such as with rilonacept, canakinumab, or anakinra), anti-IL2 agent to ligand or its receptors (such as basiliximab or daclizumab), anti-CD2 agent such as alefacept, anti-CD3 agent such as muromonab-cd3, anti-CD80/86 agent such as abatacept or belatacept, anti-sphingosine-1-phosphate receptor agent such as fingolimod, anti-05 agent such as eculizumab, anti-integrin alpha4 agent such as natalizumab, anti-$\alpha_4\beta_7$ agent such as vedolizumab, anti-mTOR agent such as sirolimus or everolimus, anti-calcineurin agent such as tacrolimus, or anti-BAFF/BlyS agent (such as belimumab, VAY736, or blisibimod), leflunomide and teriflunomide. Preferably, rituximab, ofatumumab, obinutuzumab, or veltuzumab, or a biosimilar version thereof. In yet another embodiment of any of the above aspects, the BTK inhibitor is injected locally into the patient to treat the condition of small areas of the body. Examples of conditions for which local injections can be used include inflammation of a bursa (bursitis of the hip, knee, elbow, or shoulder), a tendon (tendinitis, such as tennis elbow), and a joint (arthritis). Knee osteoarthritis, hip bursitis, painful foot conditions such as plantar fasciitis, and rotator cuff tendinitis may be treated by local injection of a BTK inhibitor.

In a sixth aspect, provided is a method of treating an autoimmune disease and/or inflammatory disease in a mammal which method comprises administering to the mammal in need thereof a therapeutically effective amount of a BTK inhibitor in combination with an immunosuppressive agent having slow manifestations of clinical effect. In one embodiment, the immunosuppressive agent is a biologic chosen from as interferon alpha, interferon gamma, an anti-CD20 agent (such as rituximab, ofatumumab, obinutuzumab, veltuzumab, or a biosimilar version thereof), anti-TNFalpha agent (such as entanercept, infliximab, golilumab, adalimumab, certolizumab pegol or a biosimilar version thereof), anti-IL6 agent toward ligand or its receptors (such as tocilizumab, sarilumab, olokizumab, elsililumab, or siltuximab), anti-IL17 agent to ligand or its receptors (such as secukinumab, ustekinumab, brodalumab, or ixekizumab), anti-IL1 agent to ligand or its receptors (such as with rilonacept, canakinumab, or anakinra), anti-IL2 agent to ligand or its receptors such as with basiliximab or daclizumab, anti-CD2 agent such as alefacept, anti-CD3 agent such as muromonab-cd3, anti-CD80/86 agent such as with abatacept orbelatacept, anti-CS agent such as eculizumab, anti-integrin alpha4 agent such as natalizumab, anti-$\alpha_4\beta_7$ agent such as vedolizumab, and anti-BAFF/BlyS agent (such as belimumab, VAY736, or blisibimod). Preferably, rituximab, ofatumumab, obinutuzumab, or veltuzumab, or a biosimilar version thereof.

Representative advantages of the above methods, include sparing the patient of disease activity without immunosuppression for prolonged periods that can lead to serious side effects. Additionally, the longer the acute flares and acute phases persist the more likely the disease process will progress and cause serious complications. Thus prompt remission of acute phases and acute flares will have a beneficial effect on the course of the disease, even without continued administration or maintenance of the active agents.

In another embodiment of the first, second, third, fourth, fifth, or sixth aspects and embodiments contained therein, the BTK inhibitor is a compound of Formula (I):

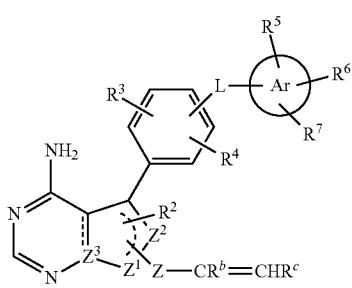

(I)

wherein:
dashed lines are an optional bond;
$Z^1$, $Z^2$, and $Z^3$ are —N— or —CH—, provided that one or two of $Z^1$, $Z^2$, and $Z^3$ are simultaneously —N—;
L is O, NR, NRCO, CONR, or NR'CONR where each R and R' is independently hydrogen or alkyl;
Ar is aryl, heteroaryl, cycloalkyl or heterocyclyl;
$R^2$ is hydrogen, alkyl, hydroxy, alkoxy, cyano, halo or haloalkyl;
$R^3$ and $R^4$ are independently hydrogen, alkyl, cyclopropyl, hydroxy, alkoxy, cyano, halo, haloalkyl or haloalkoxy;
$R^5$, $R^6$ and $R^7$ are independently hydrogen, alkyl, hydroxy, alkoxy, halo, haloalkyl, haloalkoxy, carboxy, alkoxycarbonyl, cyano, —CONH$_2$, amino, alkylamino, or dialkylamino;
Z is -alkyleneCO—, -alkyleneOCO—, -alkyleneSO$_2$—,

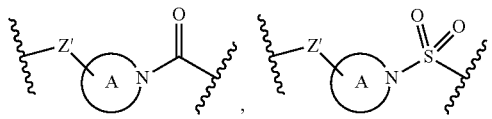

(where Z' is bond or alkylene, and ring A is heterocycloamino optionally substituted with one or two substituents independently selected from alkyl, hydroxy and fluoro, -(alkylene)-NR$^a$CO— or -(alkylene)-NR$^a$SO$_2$-(where each R$^a$ is hydrogen, alkyl or cycloalkyl);
R$^b$ is hydrogen, cyano, nitro, halo, haloalkyl, haloalkoxy, alkylthio, or alkylsulfonyl;
R$^c$ is hydrogen, alkyl, haloalkoxy, substituted alkyl, cycloalkyl, cycloalkyleneNR$^d$R$^e$ (where R$^d$ and R$^e$ are independently hydrogen, alkyl, or cycloalkyl), or 3 to 6 membered saturated monocyclic heterocyclyl containing one or two heteroatoms selected from N, O, or S and optionally substituted with one or two substituents independently selected from hydroxy, alkyl or fluoro;
and/or a pharmaceutically acceptable salt thereof;
wherein the terms are as defined below.
"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.
"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means an —SR radical where R is alkyl as defined above, e.g., methylthio, ethylthio, and the like.
"Alkylsulfonyl" means an —SO$_2$R radical where R is alkyl as defined above, e.g., methylsulfonyl, ethylsulfonyl, and the like.
"Amino" means an —NH$_2$.
"Alkylamino" means an —NHR radical where R is alkyl as defined above, e.g., methylamino, ethylamino, propylamino, or 2-propylamino, and the like.
"Alkoxy" means an —OR radical where R is alkyl as defined above, e.g., methoxy, ethoxy, propoxy, or 2-propoxy, n-, iso-, or tert-butoxy, and the like.
"Alkoxyalkyl" means a linear monovalent hydrocarbon radical of one to six carbon atoms or a branched monovalent hydrocarbon radical of three to six carbons substituted with an alkoxy group, or one or two alkoxy groups, as defined above, e.g., 2-methoxyethyl, 1-, 2-, or 3-methoxypropyl, 2-ethoxyethyl, and the like.
"Alkoxycarbonyl" means a —C(O)OR radical where R is alkyl as defined above, e.g., methoxycarbonyl, ethoxycarbonyl, and the like.
"Aryl" means a monovalent monocyclic or bicyclic aromatic hydrocarbon radical of 6 to 10 ring atoms e.g., phenyl or naphthyl.
"Cycloalkyl" means a cyclic saturated monovalent hydrocarbon radical of three to ten carbon atoms wherein one or two carbon atoms may be replaced by an oxo group, e.g., cyclopropyl, cyclobutyl, cyclopentyl, or cyclohexyl, and the like.
"Cycloalkylene" means a cyclic saturated divalent hydrocarbon radical of three to ten carbon atoms wherein one or two carbon atoms may be replaced by an oxo group, e.g., cyclopropylene, cyclobutylene, cyclopentylene, or cyclohexylene, and the like.
"Carboxy" means —COOH.
"Dialkylamino" means an —NRR' radical where R and R' are independently alkyl, as defined above.
"Halo" means fluoro, chloro, bromo, or iodo. In one embodiment halo is fluoro or chloro.
"Haloalkyl" means alkyl radical as defined above, which is substituted with a halogen atoms or one to five halogen atoms (in one embodiment fluorine or chlorine), including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it is referred to in this Application as fluoroalkyl.
"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.
"Hydroxyalkyl" means an alkyl, as defined above, substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl. In one embodiment, 2-hydroxyethyl, 2,3-dihydroxypropyl, and 1-(hydroxymethyl)-2-hydroxyethyl.
"Heterocyclyl" means a saturated or unsaturated monovalent monocyclic group of 4 to 8 ring atoms in which one or two ring atoms are heteroatoms selected from N, O, or S(O)$_n$, where n is an integer from 0 to 2, the remaining ring atoms being C. The heterocyclyl ring is optionally fused to an (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring, even though a portion of the bicycle is aromatic. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group contains a nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Heterocycloamino" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C provided that a ring atom is N. Additionally, one or two ring carbon atoms in the heterocycloamino ring can optionally be replaced by a —CO— group. When the heterocycloamino ring is unsaturated it can contain one or two ring double bonds provided that the ring is not aromatic.

"Heteroaryl" means a monovalent monocyclic or bicyclic aromatic radical of 5 to 10 ring atoms where one or more, or one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

"Oxo" or "carbonyl" means C=(O) group.

"Substituted alkyl" means alkyl group as defined herein which is substituted with one, two, or three substituents independently selected from hydroxyl, alkoxy, carboxy, cyano, carboxy, alkoxycarbonyl, alkylthio, alkylsulfonyl, halo, —CONRR' or —NRR' (where each R is hydrogen, alkyl, cycloalkyl, hydroxyalkyl, or alkoxyalkyl, and each R' is hydrogen, alkyl, or cycloalkyl), heterocyclyl (in one embodiment heterocycloamino as defined herein) which is optionally substituted with one or two groups independently selected from alkyl, hydroxyl, alkoxy, alkylthio, alkylsulfonyl, halo, or —CONRR' where R and R' are as defined above,

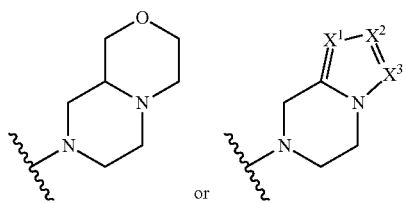

where one or two of $X^1$, $X^2$ and $X^3$ are nitrogen and the rest are carbon and the ring is optionally substituted with one or two substituents independently selected from alkyl, haloalkyl, or halo.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

In one embodiment, the compound of Formula (I) is:
2-(3-(4-amino-3-(4-phenoxyphenyl)-1H-pyrazolo[3,4-d]pyrimidin-1-yl)piperidine-1-carbonyl)-3-cyclopropylacrylonitrile;
2-(2-((4-amino-3-(4-phenoxyphenyl)-1H-pyrazolo[3,4-d]pyrimidin-1-yl)methyl)pyrrolidine-1-carbonyl)-3-cyclopropylacrylonitrile;
2-(4-(4-amino-3-(4-phenoxyphenyl)-1H-pyrazolo[3,4-d]pyrimidin-1-yl)piperidine-1-carbonyl)-3-cyclopropylacrylonitrile;
2-(3-(4-amino-3-(4-(3,4-dichlorophenoxy)-3-methoxyphenyl)-1H-pyrazolo[3,4-d]pyrimidin-1-yl)piperidine-1-carbonyl)-3-cyclopropylacrylonitrile;
2-(2-((4-amino-3-(4-(3,4-dichlorophenoxy(3-methoxyphenyl)-1H-pyrazolo[3,4-d]pyrimidin-1-yl)methyl)pyrrolidine-1-carbonyl)-3-cyclopropylacrylonitrile;
2-(4-(4-amino-3-(4-(3,4-dichlorophenoxy)-3-methoxyphenyl)-1H-pyrazolo[3,4-d]pyrimidin-1-yl)piperidine-1-carbonyl)-3-cyclopropylacrylonitrile;
2-(3-(4-amino-3-(4-phenoxyphenyl)-1H-pyrazolo[3,4-d]pyrimidin-1-yl)piperidine-1-carbonyl)-4,4-dimethylpent-2-enenitrile;
2-(4-(4-amino-3-(4-phenoxyphenyl)-1H-pyrazolo[3,4-d]pyrimidin-1-yl)piperidine-1-carbonyl)-4,4-dimethylpent-2-enenitrile;
2-(4-(4-amino-3-(4-(3,4-dichlorophenoxy)-3-methoxyphenyl)-1H-pyrazolo[3,4-d]pyrimidin-1-yl)piperidine-1-carbonyl)-4,4-dimethylpent-2-enenitrile;
2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile;
N-((1s,4s)-4-(4-amino-3-(4-phenoxyphenyl)-1H-pyrazolo[3,4-d]pyrimidin-1-yl)cyclohexyl)-2-cyano-3-cyclopropylacrylamide;
2-(2-((4-amino-3-(4-(3,4-dichlorophenoxy)-3-methoxyphenyl)-1H-pyrazolo[3,4-d]pyrimidin-1-yl)methyl)pyrrolidine-1-carbonyl)-4,4-dimethylpent-2-enenitrile;
N-((1r,4r)-4-(4-amino-3-(4-(3,4-dichlorophenoxy)-3-methoxyphenyl)-1H-pyrazolo[3,4-d]pyrimidin-1-yl)cyclohexyl)-2-cyano-3-cyclopropylacrylamide;
N-((1s,4s)-4-(4-amino-3-(4-phenoxyphenyl)-1H-pyrazolo[3,4-d]pyrimidin-1-yl)cyclohexyl)-2-cyano-4,4-dimethylpent-2-enamide;
(R)-2-(3-(4-amino-3-(4-(3-fluorophenoxy)phenyl)-1H-pyrazolo[3,4-d]pyrimidin-1-yl)piperidine-1-carbonyl)-3-cyclopropylacrylonitrile;
(S)-2-(3-(4-amino-3-(4-(3-fluorophenoxy)phenyl)-1H-pyrazolo[3,4-d]pyrimidin-1-yl)piperidine-1-carbonyl)-3-cyclopropylacrylonitrile;
N-((1r,4r)-4-(4-amino-3-(4-(3,4-dichlorophenoxy)-3-methoxyphenyl)-1H-pyrazolo[3,4-d]pyrimidin-1-yl)cyclohexyl)-2-cyano-4,4-dimethylpent-2-enamide;
(R)-2-(3-(4-amino-3-(4-(3,5-difluorophenoxy)phenyl)-1H-pyrazolo[3,4-d]pyrimidin-1-yl)piperidine-1-carbonyl)-3-cyclopropylacrylonitrile;
(S)-2-(3-(4-amino-3-(4-(3,5-difluorophenoxy)phenyl)-1H-pyrazolo[3,4-d]pyrimidin-1-yl)piperidine-1-carbonyl)-3-cyclopropylacrylonitrile;

(R)-2-(3-(4-amino-3-(2-fluoro-4-(phenoxy)phenyl)-1H-pyrazolo[3,4-d]pyrimidin-1-yl)piperidine-1-carbonyl)-3-cyclopropylacrylonitrile;

(S)-2-(3-(4-amino-3-(2-fluoro-4-(phenoxy)phenyl)-1H-pyrazolo[3,4-d]pyrimidin-1-yl)piperidine-1-carbonyl)-3-cyclopropylacrylonitrile;

2-(3-(4-amino-3-(4-(3,4-dichlorophenoxy)-3-methoxyphenyl)-1H-pyrazolo[3,4-d]pyrimidin-1-yl)piperidine-1-carbonyl)-4,4-dimethylpent-2-enenitrile;

N-((1s,4s)-4-(4-amino-3-(4-(3,4-dichlorophenoxy)-3-methoxyphenyl)-1H-pyrazolo[3,4-d]pyrimidin-1-yl)cyclohexyl)-2-cyano-3-cyclopropylacrylamide;

N-((1s,4s)-4-(4-amino-3-(4-(3,4-dichlorophenoxy)-3-methoxyphenyl)-1H-pyrazolo[3,4-d]pyrimidin-1-yl)cyclohexyl)-2-cyano-4,4-dimethylpent-2-enamide;

(R)-2-(2-((4-amino-3-(4-phenoxyphenyl)-1H-pyrazolo[3,4-d]pyrimidin-1-yl)methyl)pyrrolidine-1-carbonyl)-3-cyclopropylacrylonitrile;

(R)-2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile;

(S)-2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile;

(R)-2-(2-((4-amino-3-(4-(3-fluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(4-(3-fluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(4-(3,5-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(4-(3,5-difluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile;

2-(3-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile;

(R)-2-(3-(4-amino-3-(4-phenoxyphenyl)-1H-pyrazolo[3,4-d]pyrimidin-1-yl)piperidine-1-carbonyl)-4,4-dimethylpent-2-enenitrile;

(S)-2-(3-(4-amino-3-(4-phenoxyphenyl)-1H-pyrazolo[3,4-d]pyrimidin-1-yl)piperidine-1-carbonyl)-4,4-dimethylpent-2-enenitrile;

(R)-2-(3-(4-amino-3-(4-phenoxyphenyl)-1H-pyrazolo[3,4-d]pyrimidin-1-yl)piperidine-1-carbonyl)-3-cyclopropylacrylonitrile;

(R)-2-(2-((4-amino-3-(4-(2,3-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(4-(2,3-difluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(4-(2,6-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(4-(2,6-difluorophenoxy)phenyl)-1H-pyrazolo[3,4-d]pyrimidin-1-yl)methyl)pyrrolidine-1-carbonyl)-3-cyclopropylacrylonitrile;

(R)-2-(3-(4-amino-3-(4-(2-fluorophenoxy)phenyl)-1H-pyrazolo[3,4-d]pyrimidin-1-yl)piperidine-1-carbonyl)-3-cyclopropylacrylonitrile;

(S)-2-(3-(4-amino-3-(4-(2-fluorophenoxy)phenyl)-1H-pyrazolo[3,4-d]pyrimidin-1-yl)piperidine-1-carbonyl)-3-cyclopropylacrylonitrile;

N-(2-(4-amino-3-(4-phenoxyphenyl)-1H-pyrazolo[3,4-d]pyrimidin-1-yl)ethyl)-2-cyano-3-cyclopropylacrylamide;

(R)-2-(3-(4-amino-3-(4-(2,3-difluorophenoxy)phenyl)-1H-pyrazolo[3,4-d]pyrimidin-1-yl)piperidine-1-carbonyl)-3-cyclopropylacrylonitrile;

(S)-2-(3-(4-amino-3-(4-(2,3-difluorophenoxy)phenyl)-1H-pyrazolo[3,4-d]pyrimidin-1-yl)piperidine-1-carbonyl)-3-cyclopropylacrylonitrile;

(R)-2-(3-(4-amino-3-(4-(2,6-difluorophenoxy)phenyl)-1H-pyrazolo[3,4-d]pyrimidin-1-yl)piperidine-1-carbonyl)-3-cyclopropylacrylonitrile;

(S)-2-(3-(4-amino-3-(4-(2,6-difluorophenoxy)phenyl)-1H-pyrazolo[3,4-d]pyrimidin-1-yl)piperidine-1-carbonyl)-3-cyclopropylacrylonitrile;

(R)-2-(3-(4-amino-3-(4-(2,5-difluorophenoxy)phenyl)-1H-pyrazolo[3,4-d]pyrimidin-1-yl)piperidine-1-carbonyl)-3-cyclopropylacrylonitrile;

(S)-2-(3-(4-amino-3-(4-(2,5-difluorophenoxy)phenyl)-1H-pyrazolo[3,4-d]pyrimidin-1-yl)piperidine-1-carbonyl)-3-cyclopropylacrylonitrile;

(R)-2-(2-((4-amino-3-(4-(2-fluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(4-(2-fluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(4-(2,5-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(4-(2,5-difluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-fluoro-4-(3,5-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-fluoro-4-(3,5-difluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(3-fluoro-4-(phenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(3-fluoro-4-(phenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-fluoro-4-(2,3-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-fluoro-4-(2,3-difluorophenoxy)phenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-fluoro-4-(2,6-difluorophenoxy)phenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-fluoro-4-(2,6-difluorophenoxy)phenyl)-1H-pyrazolo[3,4-d]pyrimidin-1-yl)methyl)pyrrolidine-1-carbonyl)-3-cyclopropylacrylonitrile;

N-(2-(4-amino-3-(2-fluoro-4-phenoxyphenyl)-1H-pyrazolo[3,4-d]pyrimidin-1-yl)ethyl)-2-cyano-3-cyclopropylacrylamide;

N-(2-(4-amino-3-(2-fluoro-4-phenoxyphenyl)-1H-pyrazolo[3,4-d]pyrimidin-1-yl)-2-methylpropyl)-2-cyano-3-cyclopropylacrylamide;

N-(1-(4-amino-3-(2-fluoro-4-phenoxyphenyl)-1H-pyrazolo[3,4-d]pyrimidin-1-yl)-2-methylpropan-2-yl)-2-cyano-3-cyclopropylacrylamide;

N-(2-(4-amino-3-(2-fluoro-4-phenoxyphenyl)-1H-pyrazolo[3,4-d]pyrimidin-1-yl)ethyl)-1-cyano-2-cyclopropylethenesulfonamide;

N-(2-(4-amino-3-(2-fluoro-4-phenoxyphenyl)-1H-pyrazolo[3,4-d]pyrimidin-1-yl)ethyl)-1-cyano-2-cyclopropyl-N-methylethenesulfonamide;

2-(4-amino-3-(2-fluoro-4-phenoxyphenyl)-1H-pyrazolo[3,4-d]pyrimidin-1-yl)ethyl 2-cyano-3-cyclopropylacrylate;

1-(4-amino-3-(2-fluoro-4-phenoxyphenyl)-1H-pyrazolo[3,4-d]pyrimidin-1-yl)-2-methylpropan-2-yl 2-cyano-3-cyclopropylacrylate;

2-((2-(4-amino-3-(2-fluoro-4-phenoxyphenyl)-1H-pyrazolo[3,4-d]pyrimidin-1-yl)ethyl)sulfonyl)-3-cyclopropylacrylonitrile;

2-(5-((4-amino-3-(2-fluoro-4-phenoxyphenyl)-1H-pyrazolo[3,4-d]pyrimidin-1-yl)methyl)oxazol-2-yl)-3-cyclopropylacrylonitrile;

(R)-2-(3-(4-amino-5-(4-phenoxyphenyl)-7H-pyrrolo[2,3-d]pyrimidin-7-yl)piperidine-1-carbonyl)-3-cyclopropylacrylonitrile;

(S)-2-(3-(4-amino-5-(4-phenoxyphenyl)-7H-pyrrolo[2,3-d]pyrimidin-7-yl)piperidine-1-carbonyl)-3-cyclopropylacrylonitrile;

(R)-2-(3-(4-amino-5-(4-(3,5-difluorophenoxy)phenyl)-7H-pyrrolo[2,3-d]pyrimidin-7-yl)piperidine-1-carbonyl)-3-cyclopropylacrylonitrile;

(S)-2-(3-(4-amino-5-(4-(3,5-difluorophenoxy)phenyl)-7H-pyrrolo[2,3-d]pyrimidin-7-yl)piperidine-1-carbonyl)-3-cyclopropylacrylonitrile;

(R)-2-(3-(4-amino-5-(2-fluoro-4-phenoxyphenyl)-7H-pyrrolo[2,3-d]pyrimidin-7-yl)piperidine-1-carbonyl)-3-cyclopropylacrylonitrile;

(S)-2-(3-(4-amino-5-(2-fluoro-4-phenoxyphenyl)-7H-pyrrolo[2,3-d]pyrimidin-7-yl)piperidine-1-carbonyl)-3-cyclopropylacrylonitrile;

(R)-2-(2-((4-amino-5-(4-phenoxyphenyl)-7H-pyrrolo[2,3-d]pyrimidin-7-yl)methyl)pyrrolidine-1-carbonyl)-3-cyclopropylacrylonitrile;

(S)-2-(2-((4-amino-5-(4-phenoxyphenyl)-7H-pyrrolo[2,3-d]pyrimidin-7-yl)methyl)pyrrolidine-1-carbonyl)-3-cyclopropylacrylonitrile;

(R)-2-(2-((4-amino-5-(4-(3,5-difluorophenoxy)phenyl)-7H-pyrrolo[2,3-d]pyrimidin-7-yl)methyl)pyrrolidine-1-carbonyl)-3-cyclopropylacrylonitrile;

(S)-2-(2-((4-amino-5-(4-(3,5-difluorophenoxy)phenyl)-7H-pyrrolo[2,3-d]pyrimidin-7-yl)methyl)pyrrolidine-1-carbonyl)-3-cyclopropylacrylonitrile;

(R)-2-(2-((4-amino-5-(2-fluoro-4-phenoxyphenyl)-7H-pyrrolo[2,3-d]pyrimidin-7-yl)methyl)pyrrolidine-1-carbonyl)-3-cyclopropylacrylonitrile;

(S)-2-(2-((4-amino-5-(2-fluoro-4-phenoxyphenyl)-7H-pyrrolo[2,3-d]pyrimidin-7-yl)methyl)pyrrolidine-1-carbonyl)-3-cyclopropylacrylonitrile;

(R)-2-(3-(4-amino-6-methyl-5-(4-phenoxyphenyl)-7H-pyrrolo[2,3-d]pyrimidin-7-yl)piperidine-1-carbonyl)-3-cyclopropylacrylonitrile;

(S)-2-(3-(4-amino-6-methyl-5-(4-phenoxyphenyl)-7H-pyrrolo[2,3-d]pyrimidin-7-yl)piperidine-1-carbonyl)-3-cyclopropylacrylonitrile;

(R)-2-(3-(4-amino-5-(4-(3,5-difluorophenoxy)phenyl)-6-methyl-7H-pyrrolo[2,3-d]pyrimidin-7-yl)piperidine-1-carbonyl)-3-cyclopropylacrylonitrile;

(S)-2-(3-(4-amino-5-(4-(3,5-difluorophenoxy)phenyl)-6-methyl-7H-pyrrolo[2,3-d]pyrimidin-7-yl)piperidine-1-carbonyl)-3-cyclopropylacrylonitrile;

2-((3R)-3-(4-amino-5-(2-fluoro-4-phenoxyphenyl)-6-methyl-7H-pyrrolo[2,3-d]pyrimidin-7-yl)piperidine-1-carbonyl)-3-cyclopropylacrylonitrile;

2-((3S)-3-(4-amino-5-(2-fluoro-4-phenoxyphenyl)-6-methyl-7H-pyrrolo[2,3-d]pyrimidin-7-yl)piperidine-1-carbonyl)-3-cyclopropylacrylonitrile;

(R)-(2-(2-((4-amino-6-methyl-5-(4-phenoxyphenyl)-7H-pyrrolo[2,3-d]pyrimidin-7-yl)methyl)pyrrolidine-1-carbonyl)-3-cyclopropylacrylonitrile;

(S)-(2-(2-((4-amino-6-methyl-5-(4-phenoxyphenyl)-7H-pyrrolo[2,3-d]pyrimidin-7-yl)methyl)pyrrolidine-1-carbonyl)-3-cyclopropylacrylonitrile;

(R)-2-(2-((4-amino-5-(4-(3,5-difluorophenoxy)phenyl)-6-methyl-7H-pyrrolo[2,3-d]pyrimidin-7-yl)methyl)pyrrolidine-1-carbonyl)-3-cyclopropylacrylonitrile;

(S)-2-(2-((4-amino-5-(4-(3,5-difluorophenoxy)phenyl)-6-methyl-7H-pyrrolo[2,3-d]pyrimidin-7-yl)methyl)pyrrolidine-1-carbonyl)-3-cyclopropylacrylonitrile;

(R)-2-(2-((4-amino-5-(2-fluoro-4-phenoxyphenyl)-6-methyl-7H-pyrrolo[2,3-d]pyrimidin-7-yl)methyl)pyrrolidine-1-carbonyl)-3-cyclopropylacrylonitrile;

(S)-2-(2-((4-amino-5-(2-fluoro-4-phenoxyphenyl)-6-methyl-7H-pyrrolo[2,3-d]pyrimidin-7-yl)methyl)pyrrolidine-1-carbonyl)-3-cyclopropylacrylonitrile;

2-(3-((4-amino-3-(4-phenoxyphenyl)-1H-pyrazolo[3,4-d]pyrimidin-1-yl)methyl)pyrrolidine-1-carbonyl)-3-cyclopropylacrylonitrile;

N-(3-(4-amino-3-(4-phenoxyphenyl)-1H-pyrazolo[3,4-d]pyrimidin-1-yl)-2,2-dimethylpropyl)-2-cyano-3-cyclopropylacrylamide;

2-(4-(4-amino-3-(4-phenoxyphenyl)-1H-pyrazolo[3,4-d]pyrimidin-1-yl)pyridin-2-yl)-3-cyclopropylacrylonitrile;

(R)-2-(2-((4-amino-3-(2-methyl-4-phenoxyphenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-methyl-4-phenoxyphenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-chloro-4-phenoxyphenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-chloro-4-phenoxyphenyl)-1H-pyrazolo[3,4-d]pyrimidin-1-yl)methyl)pyrrolidine-1-carbonyl)-3-cyclopropylacrylonitrile;

(R)-2-(2-((4-amino-3-(4-(2,5-difluorophenoxy)phenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,5-difluorophenoxy)phenyl)-1H-pyrazolo[3,4-d]pyrimidin-1-yl)methyl)pyrrolidine-1-carbonyl)-4-methylpent-2-enenitrile;

(R)-4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;

(S)-4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;
(R)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;
(S)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4,4-dimethylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4,4-dimethylpent-2-enenitrile;
(R)-2-(2-((4-amino-3-(4-(2,6-difluorophenoxy)phenyl)-1H-pyrazolo[3,4-d]pyrimidin-1-yl)methyl)pyrrolidine-1-carbonyl)-4-methylpent-2-enenitrile;
(S)-2-(2-((4-amino-3-(4-(2,6-difluorophenoxy)phenyl)-1H-pyrazolo[3,4-d]pyrimidin-1-yl)methyl)pyrrolidine-1-carbonyl)-4-methylpent-2-enenitrile;
(R)-2-(2-((4-amino-3-(4-(2,3-difluorophenoxy)phenyl)-1H-pyrazolo[3,4-d]pyrimidin-1-yl)methyl)pyrrolidine-1-carbonyl)-4-methylpent-2-enenitrile;
(S)-2-(2-((4-amino-3-(4-(2,3-difluorophenoxy)phenyl)-1H-pyrazolo[3,4-d]pyrimidin-1-yl)methyl)pyrrolidine-1-carbonyl)-4-methylpent-2-enenitrile;
(R)-2-(2-((4-amino-6-methyl-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile;
(S)-2-(2-((4-amino-6-methyl-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile;
(R)-2-(2-((4-amino-3-(4-(2,6-difluorophenoxy)-2-fluorophenyl)-1H-pyrazolo[3,4-d]pyrimidin-1-yl)methyl)pyrrolidine-1-carbonyl)-4-methylpent-2-enenitrile;
(S)-2-(2-((4-amino-3-(4-(2,6-difluorophenoxy)-2-fluorophenyl)-1H-pyrazolo[3,4-d]pyrimidin-1-yl)methyl)pyrrolidine-1-carbonyl)-4-methylpent-2-enenitrile;
(R)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-3-cyclopropylacrylonitrile;
(S)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-3-cyclopropylacrylonitrile;
(R)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-4-methylpent-2-enenitrile;
(S)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;
(S)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;
(R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(methylamino)pent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(methylamino)pent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(dimethylamino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(dimethylamino)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(isopropylamino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(isopropylamino)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropylamino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropylamino)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-((2-methoxyethyl)amino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-((2-methoxyethyl)amino)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-ethoxy-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-ethoxy-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-aminocyclopropyl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-aminocyclopropyl)acrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(methylamino)cyclopropyl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(methylamino)cyclopropyl)acrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(ethylamino)cyclopropyl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(ethylamino)cyclopropyl)acrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(isopropylamino)cyclopropyl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(isopropylamino)cyclopropyl)acrylonitrile;

2-((S)-2-((4-amino-3-(2-fluoro-4-phenoxyphenyl)-1H-pyrazolo[3,4-d]pyrimidin-1-yl)methyl)pyrrolidine-1-carbonyl)-3-(pyrrolidin-2-yl)acrylonitrile;

2-((R)-2-((4-amino-3-(2-fluoro-4-phenoxyphenyl)-1H-pyrazolo[3,4-d]pyrimidin-1-yl)methyl)pyrrolidine-1-carbonyl)-3-(pyrrolidin-2-yl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-((dimethylamino)methyl)cyclopentyl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-((dimethylamino)methyl)cyclopentyl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-methylpiperidin-4-yl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-methylpiperidin-4-yl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(tetrahydro-2H-pyran-4-yl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(tetrahydro-2H-pyran-4-yl)acrylonitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(piperidin-4-yl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(piperidin-4-yl)acrylonitrile;

2-((S)-2-((4-amino-3-(2-fluoro-4-phenoxyphenyl)-1H-pyrazolo[3,4-d]pyrimidin-1-yl)methyl)pyrrolidine-1-carbonyl)-3-(piperidin-3-yl)acrylonitrile;

2-((R)-2-((4-amino-3-(2-fluoro-4-phenoxyphenyl)-1H-pyrazolo[3,4-d]pyrimidin-1-yl)methyl)pyrrolidine-1-carbonyl)-3-(piperidin-3-yl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4,4-dimethylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4,4-dimethylpent-2-enenitrile;

(S)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;

(R)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-(methylamino)pent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-(methylamino)pent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(dimethylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(dimethylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(ethylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(ethylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(isopropylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(isopropylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(cyclopropylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(cyclopropylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-((2-methoxyethyl)amino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-((2-methoxyethyl)amino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-ethoxy-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-ethoxy-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-aminocyclopropyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-aminocyclopropyl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(methylamino)cyclopropyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(methylamino)cyclopropyl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(ethylamino)cyclopropyl)acrylonitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(ethylamino)cyclopropyl)acrylonitrile;
(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(isopropylamino)cyclopropyl)acrylonitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(isopropylamino)cyclopropyl)acrylonitrile;
2-((S)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(pyrrolidin-2-yl)acrylonitrile;
2-((R)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(pyrrolidin-2-yl)acrylonitrile;
(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-morpholinopent-2-enenitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-morpholinopent-2-enenitrile;
(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((diethylamino)methyl)cyclopentyl)-acrylonitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((diethylamino)methyl)cyclopentyl)-acrylonitrile;
(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((dimethylamino)methyl)-cyclopentyl)acrylonitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((dimethylamino)-methyl)-cyclopentyl)acrylonitrile;
(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-methylpiperidin-4-yl)acrylonitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-methylpiperidin-4-yl)acrylonitrile;
(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(tetrahydro-2H-pyran-4-yl)acrylonitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(tetrahydro-2H-pyran-4-yl)acrylonitrile;
(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-4-yl)acrylonitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-4-yl)acrylonitrile;
2-((S)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-3-yl)acrylonitrile;
2-((R)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-3-yl)acrylonitrile;
(R)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;
(R)-4-amino-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;
(S)-4-amino-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-methyl-4-(methylamino)pent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-methyl-4-(methylamino)pent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-(dimethylamino)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-(dimethylamino)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-(ethylamino)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-(ethylamino)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-(isopropylamino)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-(isopropylamino)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-(cyclopropylamino)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-(cyclopropylamino)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-((2-methoxyethyl)amino)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-((2-methoxyethyl)amino)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-aminocyclopropyl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-aminocyclopropyl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-(methylamino)cyclopropyl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-(methylamino)cyclopropyl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-(ethylamino)cyclopropyl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-(ethylamino)cyclopropyl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-(isopropylamino)cyclopropyl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-(isopropylamino)cyclopropyl)acrylonitrile;

2-((R)-3-(4-amino-3-(2-fluoro-4-phenoxyphenyl)-1H-pyrazolo[3,4-d]pyrimidin-1-yl)piperidine-1-carbonyl)-3-(pyrrolidin-2-yl)acrylonitrile;

2-((S)-3-(4-amino-3-(2-fluoro-4-phenoxyphenyl)-1H-pyrazolo[3,4-d]pyrimidin-1-yl)piperidine-1-carbonyl)-3-(pyrrolidin-2-yl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-((diethylamino)methyl)-cyclopentyl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-((diethylamino)methyl)-cyclopentyl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-((dimethylamino)methyl)cyclopentyl)-acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-((dimethylamino)methyl)cyclopentyl)-acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(1-methylpiperidin-4-yl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(1-methylpiperidin-4-yl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(tetrahydro-2H-pyran-4-yl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(tetrahydro-2H-pyran-4-yl)acrylonitrile;

(R)-2-(3-(4-amino-3-(2-fluoro-4-phenoxyphenyl)-1H-pyrazolo[3,4-d]pyrimidin-1-yl)piperidine-1-carbonyl)-3-(piperidin-4-yl)acrylonitrile;

(S)-2-(3-(4-amino-3-(2-fluoro-4-phenoxyphenyl)-1H-pyrazolo[3,4-d]pyrimidin-1-yl)piperidine-1-carbonyl)-3-(piperidin-4-yl)acrylonitrile;

2-((R)-3-(4-amino-3-(2-fluoro-4-phenoxyphenyl)-1H-pyrazolo[3,4-d]pyrimidin-1-yl)piperidine-1-carbonyl)-3-(piperidin-3-yl)acrylonitrile;

2-((S)-3-(4-amino-3-(2-fluoro-4-phenoxyphenyl)-1H-pyrazolo[3,4-d]pyrimidin-1-yl)piperidine-1-carbonyl)-3-(piperidin-3-yl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-cyclopropylacrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-cyclopropylacrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4,4-dimethylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4,4-dimethylpent-2-enenitrile;

(R)-4-amino-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(S)-4-amino-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-(methylamino)pent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-(methylamino)pent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(ethylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(ethylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(isopropylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(isopropylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(cyclopropylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(cyclopropylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-((2-methoxyethyl)amino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-((2-methoxyethyl)amino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-ethoxy-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-ethoxy-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-aminocyclopropyl)-acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-aminocyclopropyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(methylamino)cyclopropyl)-acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(methylamino)cyclopropyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(ethylamino)cyclopropyl)-acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(ethylamino)cyclopropyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(isopropylamino)-cyclopropyl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(isopropylamino)-cyclopropyl)acrylonitrile;

2-((R)-3-(4-amino-3-(4-(2,3-difluorophenoxy)-2-fluorophenyl)-1H-pyrazolo[3,4-d]pyrimidin-1-yl)piperidine-1-carbonyl)-3-(pyrrolidin-2-yl)acrylonitrile;

2-((S)-3-(4-amino-3-(4-(2,3-difluorophenoxy)-2-fluorophenyl)-1H-pyrazolo[3,4-d]pyrimidin-1-yl)piperidine-1-carbonyl)-3-(pyrrolidin-2-yl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-morpholinopent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-morpholinopent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((diethylamino)methyl)-cyclopentyl)-acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((diethylamino)methyl)-cyclopentyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((dimethylamino)-methyl)cyclopentyl)-acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((dimethylamino)-methyl)cyclopentyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-methylpiperidin-4-yl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-methylpiperidin-4-yl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(tetrahydro-2H-pyran-4-yl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(tetrahydro-2H-pyran-4-yl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(piperidin-4-yl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(piperidin-4-yl)acrylonitrile;

2-((R)-3-(4-amino-3-(4-(2,3-difluorophenoxy)-2-fluorophenyl)-1H-pyrazolo[3,4-d]pyrimidin-1-yl)piperidine-1-carbonyl)-3-(piperidin-3-yl)acrylonitrile;

2-((S)-3-(4-amino-3-(4-(2,3-difluorophenoxy)-2-fluorophenyl)-1H-pyrazolo[3,4-d]pyrimidin-1-yl)piperidine-1-carbonyl)-3-(piperidin-3-yl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;

(R)-2-(2-((4-amino-5-(2-fluoro-4-phenoxyphenyl)-7H-pyrrolo[2,3-d]pyrimidin-7-yl)methyl)pyrrolidine-1-carbonyl)-4-(dimethylamino)-4-methylpent-2-enenitrile;

(S)-2-(2-((4-amino-5-(2-fluoro-4-phenoxyphenyl)-7H-pyrrolo[2,3-d]pyrimidin-7-yl)methyl)pyrrolidine-1-carbonyl)-4-(dimethylamino)-4-methylpent-2-enenitrile;

(R)-2-(2-((4-amino-5-(4-(2,3-difluorophenoxy)phenyl)-7H-pyrrolo[2,3-d]pyrimidin-7-yl)methyl)pyrrolidine-1-carbonyl)-3-cyclopropylacrylonitrile;

(S)-2-(2-((4-amino-5-(4-(2,3-difluorophenoxy)phenyl)-7H-pyrrolo[2,3-d]pyrimidin-7-yl)methyl)pyrrolidine-1-carbonyl)-3-cyclopropylacrylonitrile;

(R)-2-(2-((4-amino-5-(4-(2,3-difluorophenoxy)phenyl)-7H-pyrrolo[2,3-d]pyrimidin-7-yl)methyl)pyrrolidine-1-carbonyl)-4-methylpent-2-enenitrile;

(S)-2-(2-((4-amino-5-(4-(2,3-difluorophenoxy)phenyl)-7H-pyrrolo[2,3-d]pyrimidin-7-yl)methyl)pyrrolidine-1-carbonyl)-4-methylpent-2-enenitrile;

(R)-2-(2-((4-amino-5-(4-(2,3-difluorophenoxy)phenyl)-7H-pyrrolo[2,3-d]pyrimidin-7-yl)methyl)pyrrolidine-1-carbonyl)-4,4-dimethylpent-2-enenitrile;

(S)-2-(2-((4-amino-5-(4-(2,3-difluorophenoxy)phenyl)-7H-pyrrolo[2,3-d]pyrimidin-7-yl)methyl)pyrrolidine-1-carbonyl)-4,4-dimethylpent-2-enenitrile;

(R)-2-(2-((4-amino-5-(4-(2,3-difluorophenoxy)phenyl)-7H-pyrrolo[2,3-d]pyrimidin-7-yl)methyl)pyrrolidine-1-carbonyl)-4-(dimethylamino)-4-methylpent-2-enenitrile;

(S)-2-(2-((4-amino-5-(4-(2,3-difluorophenoxy)phenyl)-7H-pyrrolo[2,3-d]pyrimidin-7-yl)methyl)pyrrolidine-1-carbonyl)-4-(dimethylamino)-4-methylpent-2-enenitrile;

(R)-2-(2-((4-amino-5-(4-phenoxyphenyl)-7H-pyrrolo[2,3-d]pyrimidin-7-yl)methyl)-pyrrolidine-1-carbonyl)-4-(dimethylamino)-4-methylpent-2-enenitrile;

(S)-2-(2-((4-amino-5-(4-phenoxyphenyl)-7H-pyrrolo[2,3-d]pyrimidin-7-yl)methyl)-pyrrolidine-1-carbonyl)-4-(dimethylamino)-4-methylpent-2-enenitrile;

(R)-2-(2-((4-amino-5-(4-phenoxyphenyl)-7H-pyrrolo[2,3-d]pyrimidin-7-yl)methyl)-pyrrolidine-1-carbonyl)-4-methylpent-2-enenitrile;

(S)-2-(2-((4-amino-5-(4-phenoxyphenyl)-7H-pyrrolo[2,3-d]pyrimidin-7-yl)methyl)-pyrrolidine-1-carbonyl)-4-methylpent-2-enenitrile;

(R)-4-amino-2-(2-((4-amino-5-(2-fluoro-4-phenoxyphenyl)-7H-pyrrolo[2,3-d]-pyrimidin-7-yl)methyl)pyrrolidine-1-carbonyl)-4-methylpent-2-enenitrile;

(S)-4-amino-2-(2-((4-amino-5-(2-fluoro-4-phenoxyphenyl)-7H-pyrrolo[2,3-d]-pyrimidin-7-yl)methyl)pyrrolidine-1-carbonyl)-4-methylpent-2-enenitrile;

(R)-2-(2-((4-amino-5-(4-phenoxyphenyl)-7H-pyrrolo[2,3-d]pyrimidin-7-yl)-methyl)pyrrolidine-1-carbonyl)-4-(dimethylamino)-4-methylpent-2-enenitrile;

(S)-2-(2-((4-amino-5-(4-phenoxyphenyl)-7H-pyrrolo[2,3-d]pyrimidin-7-yl)-methyl)pyrrolidine-1-carbonyl)-4-(dimethylamino)-4-methylpent-2-enenitrile;

(R)-2-(2-((4-amino-5-(4-phenoxyphenyl)-7H-pyrrolo[2,3-d]pyrimidin-7-yl)-methyl)pyrrolidine-1-carbonyl)-4-methyl-4-morpholinopent-2-enenitrile (S)-2-(2-((4-amino-5-(4-phenoxyphenyl)-7H-pyrrolo[2,3-d]pyrimidin-7-yl)-methyl)pyrrolidine-1-carbonyl)-4-methyl-4-morpholinopent-2-enenitrile;

(R)-2-(2-((4-amino-5-(4-phenoxyphenyl)-7H-pyrrolo[2,3-d]pyrimidin-7-yl)-methyl)pyrrolidine-1-carbonyl)-4-(diethylamino)-4-methylpent-2-enenitrile;

(S)-2-(2-((4-amino-5-(4-phenoxyphenyl)-7H-pyrrolo[2,3-d]pyrimidin-7-yl)-methyl)pyrrolidine-1-carbonyl)-4-(diethylamino)-4-methylpent-2-enenitrile;

(R)-2-(2-((4-amino-5-(4-phenoxyphenyl)-7H-pyrrolo[2,3-d]pyrimidin-7-yl)-methyl)pyrrolidine-1-carbonyl)-4-ethoxy-4-methylpent-2-enenitrile;

(S)-2-(2-((4-amino-5-(4-phenoxyphenyl)-7H-pyrrolo[2,3-d]pyrimidin-7-yl)-methyl)pyrrolidine-1-carbonyl)-4-ethoxy-4-methylpent-2-enenitrile;

(R)—N-(1-(4-amino-3-(2-fluoro-4-phenoxyphenyl)-1H-pyrazolo[3,4-d]pyrimidin-1-yl)-propan-2-yl)-2-cyano-4,4-dimethylpent-2-enamide;

(S)—N-(1-(4-amino-3-(2-fluoro-4-phenoxyphenyl)-1H-pyrazolo[3,4-d]pyrimidin-1-yl)propan-2-yl)-2-cyano-4,4-dimethylpent-2-enamide;

(R)—N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;

(S)—N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;

(R)—N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide;

(S)—N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide;

(R)—N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide;

(S)—N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide;

2-((R)-2-((4-amino-3-(2-fluoro-4-phenoxyphenyl)-1H-pyrazolo[3,4-d]pyrimidin-1-yl)methyl)pyrrolidine-1-carbonyl)-3-((S)-pyrrolidin-2-yl)acrylonitrile;

2-((R)-2-((4-amino-3-(2-fluoro-4-phenoxyphenyl)-1H-pyrazolo[3,4-d]pyrimidin-1-yl)methyl)pyrrolidine-1-carbonyl)-3-((R)-pyrrolidin-2-yl)acrylonitrile;

(R)-4-amino-N-(1-(4-amino-3-(2-fluoro-4-phenoxyphenyl)-1H-pyrazolo[3,4-d]-pyrimidin-1-yl)propan-2-yl)-2-cyano-4-methylpent-2-enamide;

(S)-4-amino-N-(1-(4-amino-3-(2-fluoro-4-phenoxyphenyl)-1H-pyrazolo[3,4-d]-pyrimidin-1-yl)propan-2-yl)-2-cyano-4-methylpent-2-enamide;

N-(2-(4-amino-3-(4-phenoxyphenyl)-1H-pyrazolo[3,4-d]pyrimidin-1-yl)ethyl)-2-cyano-3-cyclopropyl-N-methylacrylamide;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;

(S)—N-(1-(4-amino-3-(2-fluoro-4-phenoxyphenyl)-1H-pyrazolo[3,4-d]pyrimidin-1-yl)propan-2-yl)-2-cyano-4,4-dimethylpent-2-enamide;

(S)—N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;

(S)—N—O-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide;

(S)—N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide;

(S)-4-amino-N-(1-(4-amino-3-(2-fluoro-4-phenoxyphenyl)-1H-pyrazolo[3,4-d]-pyrimidin-1-yl)propan-2-yl)-2-cyano-4-methylpent-2-enamide;

(S)—N-(1-(4-amino-3-(2-fluoro-4-phenoxyphenyl)-1H-pyrazolo[3,4-d]pyrimidin-1-yl)propan-2-yl)-2-cyano-3-cyclopropylacrylamide;

2-[(2S)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-methylpiperazin-1-yl)pent-2-enenitrile;

2-[(2R)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-methylpiperazin-1-yl)pent-2-enenitrile;

2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-piperazin-1-yl-pent-2-enenitrile;

2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-piperazin-1-yl-pent-2-enenitrile;

2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-[methyl(oxetan-3-yl)amino]pent-2-enenitrile;

2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-[methyl(oxetan-3-yl)amino]pent-2-enenitrile;

2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-(oxetan-3-ylamino)pent-2-enenitrile;

2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-(oxetan-3-ylamino)pent-2-enenitrile;

2-[(3R)-3-[4-amino-3-(2-fluoro-4-phenoxy-phenyl)pyrazolo[3,4-d]pyrimidin-1-yl]piperidine-1-carbonyl]-4-methyl-4-[methyl(oxetan-3-yl)amino]pent-2-enenitrile;

2-[(3S)-3-[4-amino-3-(2-fluoro-4-phenoxy-phenyl)pyrazolo[3,4-d]pyrimidin-1-yl]piperidine-1-carbonyl]-4-methyl-4-[methyl(oxetan-3-yl)amino]pent-2-enenitrile;

2-[[(3R)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-methylpiperazin-1-yl)pent-2-enenitrile;

2-[[(3S)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-methylpiperazin-1-yl)pent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-methyl-4-(piperazin-1-yl)pent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-methyl-4-(piperazin-1-yl)pent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethyl(oxetan-3-yl)amino)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethyl(oxetan-3-yl)amino)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(ethyl(oxetan-3-yl)amino)pent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(ethyl(oxetan-3-yl)amino)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(2-oxa-6-azaspiro[3.3]heptan-6-yl)pent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(2-oxa-6-azaspiro[3.3]heptan-6-yl)pent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(2-oxa-6-azaspiro[3.3]heptan-6-yl)pent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(2-oxa-6-azaspiro[3.3]heptan-6-yl)pent-2-enenitrile;

2-[(2S)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-ethylpiperazin-1-yl)pent-2-enenitrile;

2-[(2R)-2-[[4-amino-3-(2-fluoro-4-phenoxyphenyl)pyrazolo[3,4-d]pyrimidin-1-yl]-methyl]pyrrolidine-1-carbonyl]-4-methyl-4-(4-ethylpiperazin-1-yl)pent-2-enenitrile;

2-[[(3R)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-ethylpiperazin-1-yl)pent-2-enenitrile;

2-[[(3S)-3-[4-amino-3-(2-fluoro-4-phenoxyphenyl)-1H-pyrazolo[3,4-d]-pyrimidin-1-yl]-piperidin-1-yl]carbonyl]-4-methyl-4-(4-ethylpiperazin-1-yl)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(oxetan-3-yl)aminopent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(oxetan-3-yl)aminopent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropyl(oxetan-3-yl)amino)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropyl(oxetan-3-yl)amino)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(cyclopropyl(oxetan-3-yl)amino)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(cyclopropyl(oxetan-3-yl)amino)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(4-isopropylpiperazin-1-yl)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(4-isopropylpiperazin-1-yl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(4-(tert-butyl)piperazin-1-yl)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(4-(tert-butyl)piperazin-1-yl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(4-(2-methoxyethyl)piperazin-1-yl)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(4-(2-methoxyethyl)piperazin-1-yl)-4-methylpent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-((R)-hexahydropyrazino[2,1-c][1,4]oxazin-8(1H)-yl)-4-methylpent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-((R)-hexahydropyrazino[2,1-c][1,4]oxazin-8(1H)-yl)-4-methylpent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-((S)-hexahydropyrazino[2,1-c][1,4]oxazin-8(1H)-yl)-4-methylpent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-((S)-hexahydropyrazino[2,1-c][1,4]oxazin-8(1H)-yl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(2,2,2-trifluoroethyl)piperazin-1-yl)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(2,2,2-trifluoroethyl)piperazin-1-yl)pent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-methyl-4-((3S,5R)-3,4,5-trimethylpiperazin-1-yl)pent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-methyl-4-((3S,5R)-3,4,5-trimethylpiperazin-1-yl)pent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-((3S,5R)-3,5-dimethylpiperazin-1-yl)-4-methylpent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-((3S,5R)-3,5-dimethylpiperazin-1-yl)-4-methylpent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-((2R,5S)-2,5-dimethylpiperazin-1-yl)-4-methylpent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-((2R,5S)-2,5-dimethylpiperazin-1-yl)-4-methylpent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-methyl-4-((2R,5S)-2,4,5-trimethylpiperazin-1-yl)pent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-methyl-4-((2R,5S)-2,4,5-trimethylpiperazin-1-yl)pent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-((2S,5R)-2,5-dimethylpiperazin-1-yl)-4-methylpent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-((2S,5R)-2,5-dimethylpiperazin-1-yl)-4-methylpent-2-enenitrile;

2-((R)-3-(4-amino-3-(2-fluoro-4-phenoxyphenyl)-1H-pyrazolo[3,4-d]pyrimidin-1-yl)piperidine-1-carbonyl)-4-methyl-4-((2S,5R)-2,4,5-trimethylpiperazin-1-yl)pent-2-enenitrile;

2-((S)-3-(4-amino-3-(2-fluoro-4-phenoxyphenyl)-1H-pyrazolo[3,4-d]pyrimidin-1-yl)piperidine-1-carbonyl)-4-methyl-4-((2S,5R)-2,4,5-trimethylpiperazin-1-yl)pent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-(5,6-dihydroimidazo[1,2-a]pyrazin-7(8H)-yl)-4-methylpent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-(5,6-dihydroimidazo[1,2-a]pyrazin-7(8H)-yl)-4-methylpent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(methylsulfonyl)piperazin-1-yl)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(methylsulfonyl)piperazin-1-yl)pent-2-enenitrile;

(R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-methyl-3-oxopiperazin-1-yl)pent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4-methyl-4-(4-methyl-3-oxopiperazin-1-yl)pent-2-enenitrile;

(R)-4-(4-acetylpiperazin-1-yl)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;

(S)-4-(4-acetylpiperazin-1-yl)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;

(R)-methyl 4-(5-(3-(4-amino-3-(2-fluoro-4-phenoxyphenyl)-1H-pyrazolo[3,4-d]pyrimidin-1-yl)piperidin-1-yl)-4-cyano-2-methyl-5-oxopent-3-en-2-yl)piperazine-1-carboxylate;

(S)-methyl 4-(5-(3-(4-amino-3-(2-fluoro-4-phenoxyphenyl)-1H-pyrazolo[3,4-d]pyrimidin-1-yl)piperidin-1-yl)-4-cyano-2-methyl-5-oxopent-3-en-2-yl)piperazine-1-carboxylate;

(R)-2-(3-(4-amino-3-(2-fluoro-4-phenoxyphenyl)-1H-pyrazolo[3,4-d]pyrimidin-1-yl)piperidine-1-carbonyl)-4,4-dimethyl-5-morpholinopent-2-enenitrile;

(S)-2-(3-(4-amino-3-(2-fluoro-4-phenoxyphenyl)-1H-pyrazolo[3,4-d]pyrimidin-1-yl)piperidine-1-carbonyl)-4,4-dimethyl-5-morpholinopent-2-enenitrile;

or a mixture of R and S isomers thereof;

or an individual E or Z isomer of any of the above compounds; and/or a pharmaceutically acceptable salt of any of the above compounds.

In another embodiment of the first, second, third, fourth, fifth, or sixth aspects and embodiments contained therein, the BTK inhibitor is a compound of formula (Ia) or (Ib) disclosed on pages 4-6, and specific compounds disclosed on pages 57-94, of PCT application publication no. WO 2009/158571, the disclosure of those pages relating to the BTK inhibitor is incorporated herein by reference in their entirety. The scope of the terms in compound for formula (Ia) and (Ib) are disclosed on pages 4-6 are as defined on pages 6-14 of WO 2009/158571, the disclosure of those pages relating to definitions is incorporated herein by reference in their entirety. In one embodiment, the compound is N-(3-((5-fluoro-2-((4-(2-methoxyethoxy)phenyl)amino)-pyrimidin-4-yl)amino)phenyl)acrylamide and/or a pharmaceutically acceptable salt thereof.

In another embodiment of the first, second, third, fourth, fifth, or sixth aspects and embodiments contained therein, the BTK inhibitors are compounds of formula (I) disclosed on pages 1 and 2, paragraph [0005] and the specific compound disclosed on page 3, paragraph [0008] of PCT application publication no. WO 2013/173518, the disclosure of those pages relating to the BTK inhibitor is incorporated herein by reference in their entirety. The scope of the terms in formula (I) is disclosed on pages 1 and 2 as defined on pages 4-7, paragraphs [0013]-[0031] of WO 2013/173518 and the disclosure of those pages relating to scope of the terms is incorporated herein by reference in their entirety.

In another embodiment of the first, second, third, fourth, fifth, or sixth aspects and embodiments contained therein, the BTK inhibitors are compounds of formula (I) disclosed on pages 2 and 3, paragraph [0007], formula (Ia), paragraph [0014] disclosed on pages 5 and 6, formula (Ib), paragraph [0021] disclosed on pages 7-9, formula (II) on pages 12-13, paragraph [0043], formula (III) on pages 65-66, paragraph [00250], and formula (IV) disclosed on pages 75-76, paragraph [00272], and the specific compound disclosed on pages 80-85 and pages 165-175 of PCT application publication no. WO 2013/102059, the disclosure of those pages relating to BTK inhibitors is incorporated herein by reference in their entirety. The scope of the terms used to define the compounds of formulae (I), (Ia), (II), (III) and (IV) are as defined on pages 26-35, paragraphs [00104]-[00163], [00167], [00177] of WO 2013/102059 and the disclosure of those pages relating to scope is incorporated herein by reference in their entirety.

In another embodiment of the first, second, third, fourth, fifth, or sixth aspects and embodiments contained therein, the BTK inhibitors are compounds of formula (I) disclosed on pages 2 and 3, paragraph [0007], formula (Ia) disclosed on pages 46-48, paragraph [00207], formula (Ib) disclosed on pages 51-53, paragraph [00218], formula (III) on pages 4-5, paragraph [0009], formula (II) on pages 57 and 58, paragraph [00229], and formula (IV) disclosed on pages 63-65, paragraph [00249], and the specific compound disclosed on pages 66-75 of PCT application publication no. WO 2014/078578, the disclosure of those pages relating to BTK inhibitors is incorporated herein by reference in their entirety. The scope of the terms used to define the compounds of formulae (I), (Ia), (II), (III) and (IV) are as defined on pages 18-28, paragraphs [0066]-[00133], [00137], [00147] of WO 2014/078578 and the disclosure of those pages relating to scope is incorporated herein by reference in their entirety.

In another embodiment of the first, second, third, fourth, fifth, or sixth aspects and embodiments contained therein, the BTK inhibitor is a compound of formula (I) disclosed on pages 2 and 3, paragraph [0007], formula (II) disclosed on pages 6 and 7, paragraph [0014], formula (III) on pages 8-10, paragraph [0019], formula (Ia) disclosed on pages 50-52, paragraph [00219], formula (Ib) disclosed on pages 54-56, paragraph [00228], formula (II), page 58-60, paragraph [00237], formula (IIa) disclosed on pages 63-65, paragraph [00247], formula (IIb) disclosed on pages 67-69, paragraph [00255], formula (III), page 71-73, paragraph [00263], formula (IIIa) disclosed on pages 77-79, paragraph [00277], formula (IIIb) disclosed on pages 82-83, paragraph [00286], formula (IIIc) disclosed on pages 86-87, paragraph [00295], and the specific compound disclosed on pages 91-102 of PCT application publication no. WO 2013/116382, the disclosure of those pages relating to BTK inhibitor is incorporated herein by reference in their entirety. The scope of the terms used to define the compounds of formulae (I), (Ia), (Ib), (II), (IIa), (IIb), (III), (IIIa), (IIIb) and (IIIc) are as defined on pages 25-36, paragraphs [0088]-[00155], [00164], of WO 2013/116382 and the disclosure of those pages relating to scope is incorporated herein by reference in their entirety.

In another embodiment of the first, second, third, fourth, fifth, or sixth aspects and embodiments contained therein, the BTK inhibitor is a compound of formula (A) disclosed on pages 25 and 26, paragraph [00185], formula (B) disclosed on pages 26 and 27, paragraph [00186], formula (C) on pages 27-28, paragraph [00189], formula (D) disclosed on page 28-29, paragraph [00196], and the specific compound disclosed on pages 30-31, of PCT application publication no. WO 2008/039218, the disclosure of those pages relating to BTK inhibitor is incorporated herein by reference in their entirety. The scope of the terms in compounds of formulae (A), (B), (C), and (D) are as defined on pages 11-17 of WO 2008/039218, paragraph [0061]-[00119], [00123], [00133], and the disclosure of those pages relating to scope is incorporated herein by reference in their entirety. In one embodiment, the compound is BTK inhibitor Ibrutinib.

In another embodiment of the first, second, and third aspects and embodiments contained therein, the BTK inhibitor is a compound of formula (I) disclosed on pages 2 and 3, paragraph [0007], formula (II), pages 4-7, paragraph [0013], formula (Ia), paragraph [00216], formula (Ib), paragraph [00227], formula (Ic), paragraph [00237], formula (Id), paragraph [00247], formula (IIa), paragraph [00271], formula (III), paragraph [00283], formula (IIIa), paragraph [00293], formula (IV), paragraph [00304], formula (IVa), paragraph [00315], and the specific compounds no. 6, 13, 17, 23, 29, 35, 43, 48, 54 and 60 of PCT application publication no. WO 2014/130693 the disclosure of those pages relating to BTK inhibitor is incorporated herein by reference in their entirety. The scope of the terms in compounds of formula (I) are defined on pages 22-32, paragraph [0079]-[00146], [00160], of WO 2014/130693 and the disclosure of those pages relating to scope is incorporated herein by reference in their entirety.

In another embodiment of the first, second, third, fourth, fifth, or sixth aspects and embodiments contained therein, the BTK inhibitor is a compound of formula (I) disclosed on pages 22-24, lines 21-11 and specific compounds disclosed in table 1 page 28-34 of PCT application publication no. WO 2013/067277, the disclosure of those pages relating to BTK inhibitor is incorporated herein by reference in their entirety. The scope of the terms used to define the compounds of formula (I) are as defined on pages 6-11, lines 25 to 28 of WO 2013/067277 and the disclosure of those pages relating to scope is incorporated herein by reference in their entirety.

In another embodiment of the first, second, third, fourth, fifth, or sixth aspects and embodiments contained therein, the BTK inhibitor is a compound of formula (I) disclosed on pages 24-26, lines 1 to 15, and specific compounds disclosed in table 1 page 34-78 of PCT application publication no. WO 2013/067274, the disclosure of those pages relating to BTK inhibitor is incorporated herein by reference in their entirety. The scope of the terms used to define the compounds of formula (I) are as defined on pages 8-13, lines 1 to 5 of WO 2013/067274 are the disclosure of those pages relating to scope is incorporated herein by reference in their entirety.

In another embodiment of the first, second, third, fourth, fifth, or sixth aspects and embodiments contained therein, the BTK inhibitor is a compound of formula (I) disclosed on pages 19-20, lines 1 to 5 and specific compounds disclosed in table 1 page 32-94 of PCT application publication no. WO 2011/140488, the disclosure of those pages relating to BTK inhibitor is incorporated herein by reference in their entirety. The scope of the terms used to define the compounds of formula (I) are as defined on pages 4-8, lines 30 to 25 of WO 2011/140488 and the disclosure of those pages relating to scope is incorporated herein by reference in their entirety.

In another embodiment of the first, second, third, fourth, fifth, or sixth aspects and embodiments contained therein, the BTK inhibitor is a compound of formula (I) disclosed on page 3, paragraph [0022] and specific compounds disclosed in table 1 pages 34-78 of US application publication no. US 2013/0217880 and specific compounds disclosed therein the disclosure of those pages relating to BTK inhibitor is incorporated herein by reference in their entirety. The scope of the terms used to define the compounds of formula (I) are as defined on pages 4-5 of US 2013/0217880 are the disclosure of those pages relating to scope is incorporated herein by reference in their entirety. In one embodiment the compound is 6-amino-9-[(3R)-1-(2-butynoyl)-3-pyrrolidinyl]-7-(4-phenylphenyl)-7,9-dihydro-8H-purin-8-one and/or a salt thereof.

In another embodiment of the first, second, third, fourth, fifth, or sixth aspects and embodiments contained therein, the BTK inhibitor is a compound of formula (I) disclosed on pages 4-14, lines 1 to 11 and specific compounds disclosed in table 1 page 33-77 of PCT application publication no. WO 2013/010380 and specific compounds disclosed therein the disclosure of those pages relating to BTK inhibitor is incorporated herein by reference in their entirety. The scope of the terms used to define the compounds of formula (I) are as defined on pages 14-23, lines 13 to 4 of WO 2013/010380 and the disclosure of those pages relating to scope is incorporated herein by reference in their entirety.

In another embodiment of the first, second, third, fourth, fifth, or sixth aspects and embodiments contained therein, the BTK inhibitor is a compound of formula (I) disclosed on pages 3-4, lines 4-28 and specific compounds disclosed in table 1 page 10-16 of PCT application publication no. WO 2013/010868 and specific compounds disclosed therein the disclosure of those pages relating to BTK inhibitor is incorporated herein by reference in their entirety. The scope of the terms used to define the compounds of formula (I) are as defined on pages 4-6, lines 30-37 of WO 2013/010868 and the disclosure of those pages relating to scope is incorporated herein by reference in their entirety.

In another embodiment of the first, second, third, fourth, fifth, or sixth aspects and embodiments contained therein, the BTK inhibitor is a compound of formula (I) disclosed on pages 3-4, lines 5 to 31 and specific compounds disclosed in table 1 page 43-47 of PCT application publication no. WO 2013/010869 and specific compounds disclosed therein the disclosure of those pages relating to BTK inhibitor is incorporated herein by reference in their entirety. The scope of the terms used to define the compounds of formula (I) are as defined on pages 4-7, lines 34 to 37 of WO 2013/010869 and the disclosure of those pages relating to scope is incorporated herein by reference in their entirety.

In another embodiment of the first, second, third, fourth, fifth, or sixth aspects and embodiments contained therein, the BTK inhibitors are those disclosed in WO2014/025976, WO2014/151620, and WO2014/152114, the disclosures of which related to BTK inhibitors are incorporated herein by reference in their entirety.

In another embodiment of the first, second, third, fourth, fifth, or sixth aspects and embodiments contained therein, the BTK inhibitor is (R,E)-2-(3-(4-amino-3-(2-fluoro-4-phenoxyphenyl)-1H-pyrazolo[3,4-d]-pyrimidin-1-yl)piperidine-1-carbonyl)-4,4-dimethylpent-2-enenitrile or an (E), or (Z) isomer thereof, Ibrutinib (Pharmacyclics/Johnson and Johnson) AVL 263 and 293 (Avila Therapeutics, Celgene Corporation), GDC-0834 (Genentech), GDC0853 (Genentech), BMS-488516 and 509744 (Bristol Myers Squibb), CGI-1746 (Gilead Sciences), CTA-056 (Genentech), HY-11066 (also CTK417891), ONO-4059 (Ono Pharmaceutical Co. Ltd), ONO-WG37 (Ono Pharmaceutical Co. Ltd), PLS-123 (Peking Univ.), RN486 (Hoffmann Las Roche), HM71224 (Hanmi Pharmceutical Co. Ltd.), or ACP-196 (Acerta Pharma BV).

In another embodiment of the first, second, third, fourth, fifth, or sixth aspects and embodiments contained therein, the BTK inhibitor is ABT-105 or ABBV-105 (AbbVie), AC0025 (ACEA Biosciences), BGB3111 (BeiGene), CC-292 (Celgene), EBI-1266 (Eternity Bioscience), MSC-2364447 (Merck Biopharma), PF-06250112 and PF-303 (Pfizer), RG7625 and RG7880 (Hoffmann La Roche), SNS-062 (Sunesis), TP-4207 (Tolero Pharmaceuticals), or X-022 (X-Chem).

In another embodiment of the first, second, third, fourth, fifth, or sixth aspects and embodiments contained therein, the BTK inhibitor is
(R)-1-(3-(4-amino-3-(4-phenoxyphenyl)-1H-pyrazolo[3,4-d]pyrimidin-1-yl)piperidin-1-yl)prop-2-en-1-one,
(R)-4-(8-amino-3-(1-(but-2-ynoyl)pyrrolidin-2-yl)imidazo[1,5-a]pyrazin-1-yl)-N-(pyridin-2-yl)benzamide,
(S)-7-(1-acryloylpiperidin-4-yl)-2-(4-phenoxyphenyl)-4,5,6,7-tetrahydropyrazolo[1,5-a]pyrimidine-3-carboxamide,
(S)-7-(1-(but-2-ynoyl)piperidin-4-yl)-2-(4-phenoxyphenyl)-4,5,6,7-tetrahydropyrazolo[1,5-a]pyrimidine-3-carboxamide,
N-(3-((2-((2-methoxy-4-(4-methylpiperazin-1-yl)phenyl)amino)thieno[3,2-d]pyrimidin-4-yl)oxy)phenyl)acrylamide,
1-(3-((2-((4-(4-methylpiperazin-1-yl)phenyl)amino)-[1,2,4]triazolo[1,5-a]pyridin-8-yl)oxy)phenyl)prop-2-en-1-one,
(R)-6-amino-9-(1-(but-2-ynoyl)pyrrolidin-3-yl)-7-(4-phenoxyphenyl)-7H-purin-8(9H)-one,
N-(2-((6-((5-(5-fluoro-2-(hydroxymethyl)-3-(4-oxo-6,7,8,9-tetrahydrobenzo[4,5]thieno[2,3-d]pyridazin-3(4H)-yl)phenyl)-1-methyl-2-oxo-1,2-dihydropyridin-3-yl)amino)pyridin-2-yl)amino)ethyl)acrylamide,
N-(3-((5-fluoro-2-((4-(2-methoxyethoxy)phenyl)amino)pyrimidin-4-yl)amino)phenyl)acrylamide,
(S)-5-amino-1-(1-cyanopiperidin-3-yl)-3-(4-(2,4-difluorophenoxy)phenyl)-1H-pyrazole-4-carboxamide,
6-(1-acryloylpiperidin-4-yl)-2-(4-phenoxyphenyl)nicotinamide, or
(R)-1-(1-acryloylpiperidin-3-yl)-4-amino-N-(5-chlorobenzo[d]oxazol-2-yl)-1H-pyrazolo[3,4-d]pyrimidine-3-carboxamide.

In another embodiment of the first, second, third, fourth, fifth, or sixth aspects and embodiments contained therein, the BTK inhibitor is chosen from:

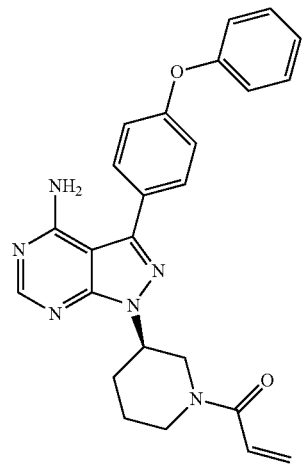

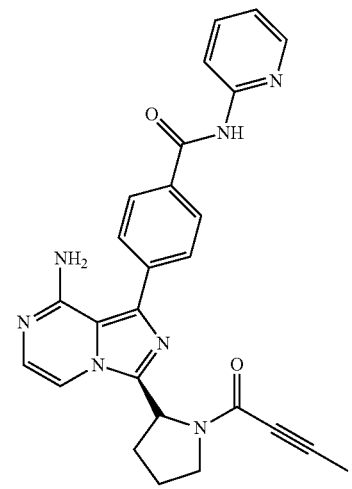

37
-continued
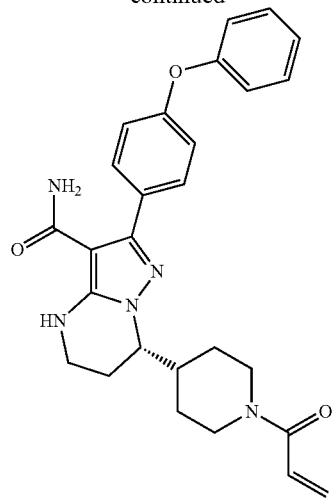
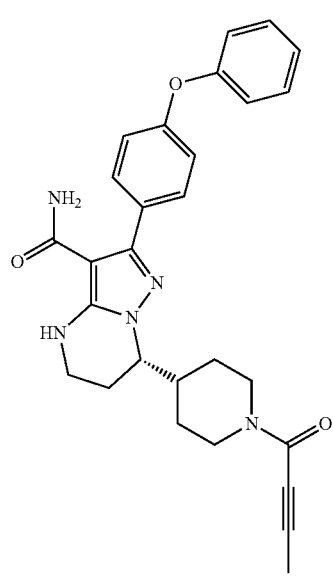
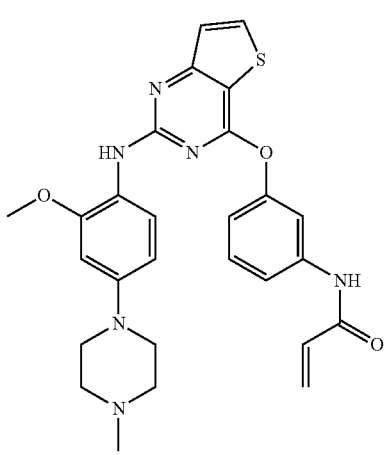
38
-continued
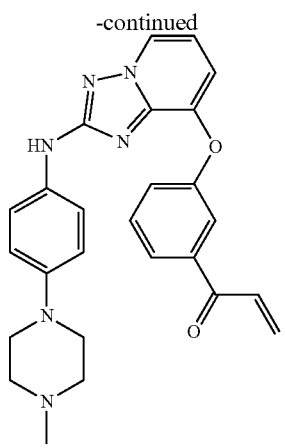
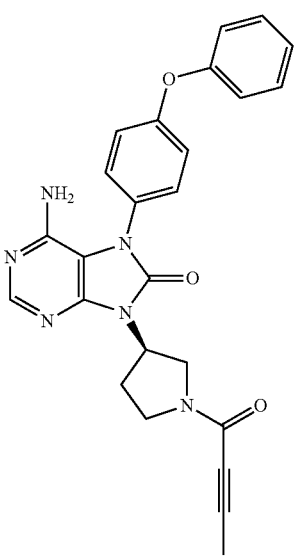
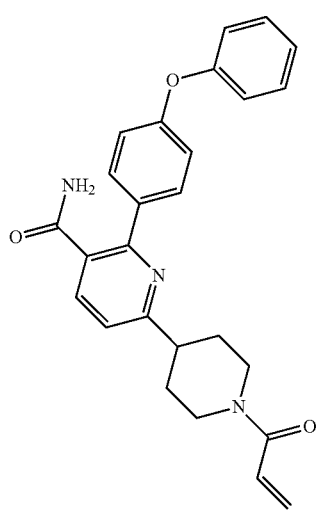

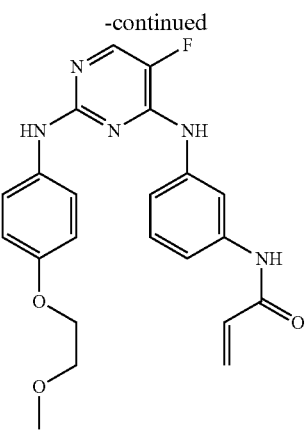

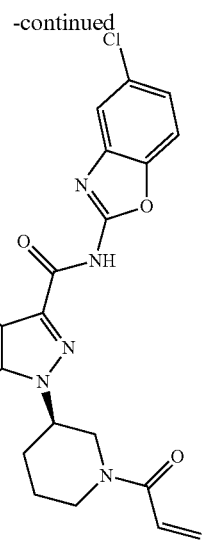

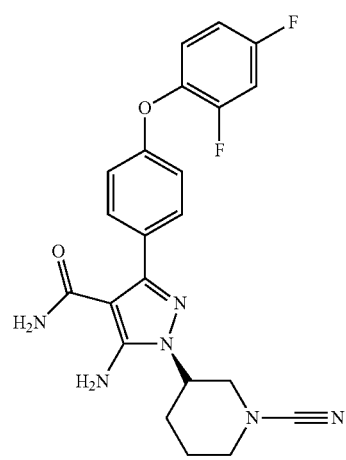

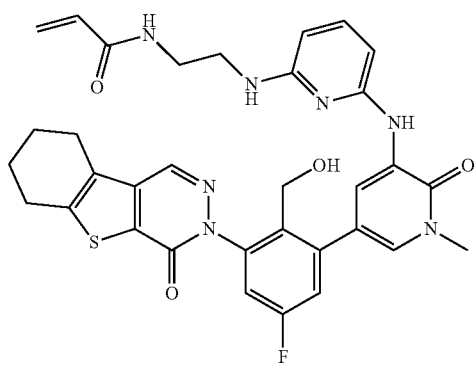

Other terms used herein have the following meaning unless stated otherwise:

"Acute" as used herein means a disease with a rapid onset and/or a short course.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, portions of which relate to suitable pharmaceutically acceptable salts are incorporated herein by reference. See also Berge at al., Pharmaceutical Salts, Journal of Pharmaceutical Sciences, 1, Volume 66, Number 1, January 1997.

Treatment decisions often follow formal or informal algorithmic guidelines. Treatment options can often be ranked or prioritized into lines of therapy: first-line therapy, second-line therapy, third-line therapy, and so on. First-line therapy is the first therapy that will be tried. Its priority over other options is usually either (1) formally recommended on the basis of clinical trial evidence for its best-available combination of efficacy, safety, and tolerability or (2) chosen based on the clinical experience of the physician. If a first-line therapy either fails to resolve the issue or produces intolerable side effects, additional (second-line) therapies may be substituted or added to the treatment regimen, followed by third-line therapies, and so on. Accordingly, "first-line" therapy as used herein means therapy usually given when someone is diagnosed with a particular disease or condition and can be categorized as standard of care.

"Maintenance therapy" as used herein means a therapy, therapeutic regimen, or course of therapy which is administered subsequent to an initial course of therapy administered to a patient with a disease. Maintenance therapy can be used to halt, slow down, or even reverse the progression of the disease, to maintain the improvement in health achieved by the initial treatment and/or enhance the gains achieved by the initial therapy.

"Flares" as used herein means an exacerbation of a chronic disease. Sometimes referred to as a flare-up, a flare occurs when symptoms of a disease that has been present for a time suddenly worsen. For example, in many arthritis conditions the joints can flare with worsening of stiffness, pain, and swelling.

The compounds of the present disclosure may have stereocenter, i.e., assymetric centers, also referenced as chiral centers. Compounds of the present disclosure containing an asymmetrically substituted atom may be isolated in optically active or racemic forms. It is well known in the art how to prepare optically active forms, such as by resolution of materials. All chiral, diastereomeric, and racemic forms are within the scope of this disclosure, unless the specific stereochemistry or isomeric form is specifically indicated.

The compounds of the present disclosure can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (I) (or any of the embodiments thereof described herein), are within the scope of this disclosure and claims appended hereto.

It will be understood by a person of ordinary skill in the art that when a compound is denoted as (R), it may contain the corresponding (S) stereoiomer as an impurity i.e., the (S) stereoisomer in less than about 1% by wt and vice versa. Accordingly, when the compound herein is denotes as a mixture of (R) and (S) stereoisomers, it means that the amount of (R) or (S) enantiomer in the mixture is greater than about 1% by wt. Similar analysis applies with when a compound is denoted as the (E) isomer, (Z) isomer or a mixture of (E) and (Z) isomers. And herein, where the term 'about' is used with a numerical value, the numerical value may vary by ±10%." Therefore, "about 1" denotes a range from 0.9 to 1.1.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. And in the specification, including the documents incorporated herein by reference, and in the claims, unless the context clearly dictates otherwise, the term "a" has its customary meaning of "one or more." Hence, "a pharmaceutically acceptable carrier/excipient," as used in the specification and claims means one or more pharmaceutically acceptable carrier/excipient.

"Treating," "treat," or "treatment" of a disease includes:
(1) inhibiting the disease, i.e., arresting or reducing the development of the disease or its clinical symptoms; or
(2) relieving the disease, i.e., causing regression of the disease or its clinical symptoms. A "therapeutically effective amount" means the amount of a compound of the present disclosure that, when administered to a mammal, such as a human, for treating a disease, is sufficient to effect such treatment for the disease. The "therapeutically effective amount" will vary depending on the compound, the disease and its severity and the age, weight, etc., of the mammal to be treated.

"Mammal" as used herein means animals such as dogs, cats, and humans, preferably humans.

Formulations and Administration

In general, the compounds of this disclosure will be administered in a therapeutically effective amount by any of the accepted modes of administration, such as oral, for agents that serve similar utilities. Therapeutically effective amounts of compounds this disclosure may range from about 0.01 to about 500 mg per kg patient body weight per day, which can be administered in single or multiple doses. A suitable dosage level may be from about 0.1 to about 250 mg/kg per day, such as about 0.5 to about 100 mg/kg per day.

A suitable dosage level may also be about 0.01 to about 250 mg/kg per day, such as about 0.05 to about 100 mg/kg per day, and further such as about 0.1 to about 50 mg/kg per day. Within this range the dosage can be about 0.05 to about 0.5, such as about 0.5 to about 5, and further such as about 5 to about 50 mg/kg per day. For oral administration, the compositions can be provided in the form of tablets containing about 1 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount to be administered of the compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. The disclosures of those two patents are incorporated by reference with respect to those portions relating to pharmaceutical formulations.

The compositions comprise, in general, a compound of this disclosure) in combination with a pharmaceutically acceptable excipient. Pharmaceutically acceptable excipients are non-toxic, aid administration, and do not adversely affect the therapeutic benefit of the compound of this disclosure. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000), incorporated by reference herein with respect to the portions relating to pharmaceutical excipients and their formulations.

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being a suitable pharmaceutical excipients. For example, the compound is present at a level of about 1-80 wt. %. With respect to the numerical range 0.01-99.99 "about" denotes less than 0.01%. With respect to the numerical range 1 to 80, "about" denotes 0.05 with respect to 1 and 10 with respect to 80, thus covering a range from 0.05 to 90 wt. %.

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously, such as fixed dose combination, or sequentially with a compound of the present disclosure. When a compound of this disclosure is used contemporaneously with one or more other drugs, a pharmaceutical composition in unit dosage form containing such other drugs and the compound of the present disclosure, i.e., a fixed dose compound, is preferred. However, the combination therapy may also include therapies in which the compound of this disclosure and one or more other drugs are administered on different overlapping schedules or even non-overlapping schedules. It is also contemplated that situations will arise that when used in combination with one or more other active ingredients, the compounds of the present disclosure and the other active ingredients may be used in lower doses than when each is used singly.

Dog Pemphigus Foliaceus Study

A 30 kg Doberman dog with a characteristic first presentation of pemphigus folliaceus on the nose and paws was administered an oral dose of 500 mg daily of the BTK inhibitor (R,E)-2-(3-(4-amino-3-(2-fluoro-4-phenoxyphenyl)-1H-pyrazolo[3,4-d]-pyrimidin-1-yl)piperidine-1-carbonyl)-4,4-dimethylpent-2-enenitrile instead of the usual treatment for pemphigus of high dose corticosteroids (typically 1-2 mg/kg). This dose resulted in a level of BTK occupancy 24 hours after each dose of approximately 70% as confirmed by blood taken 24 hours after the first dose.

The dog responded clinically to the drug as a monotherapy within three days, with improved eating and ambulation noted by the owner. At the one week follow up visit both owner and observing veterinarian reported improved general health and commencement of pemphigus lesion healing. The observing veterinarian commented that the improvement was "just like with corticosteroids" and recommended that corticosteroid therapy did not need to be commenced. No well-known corticosteroid-like adverse effects in canines, such as polyuria, polydipsia, polyphagia or weight gain, were noted.

After two weeks of treatment, the general health of the dog was excellent and skin lesions continued to improve. By four weeks, skin lesions had completely healed (see FIGS. 1A, 1B, 2A, and 2B).

The surprising conclusion of this experiment is that adequate doses of a BTK inhibitor are effective and safe as the acute treatment for pemphigus folliaceus in a dog, replacing the need for corticosteroid therapy.

As shown in Table 3, dog PF and human PV share many similar characteristics that make generalization of treatment effects for human disease from observations of the dog disease credible.

TABLE 3

| Comparison of dog pemphigus foliaceus (PF) and human pemphigus vulgaris (PV) | | |
|---|---|---|
| Naturally occurring autoimmune blistering disease | Dog PF | Human PV |
| Autoantigens to epidermal proteins | ✓ | ✓ |
| Never resolves spontaneously | ✓ | ✓ |
| Mainstay of treatment high dose corticosteroids | ✓ | ✓ |
| Early disease response to corticosteroids 1-2 weeks | ✓ | ✓ |
| Full disease control with corticosteroids takes 4-12 weeks | ✓ | ✓ |
| Relapses without maintenance treatment | ✓ | ✓ |
| High mortality in first year, partly presumed due to high dose corticosteroids | ✓ | ✓ |

In addition, the ability of (R, E)-2-(3-(4-amino-3-(2-fluoro-4-phenoxyphenyl)-1H-pyrazolo[3,4-d]-pyrimidin-1-yl)piperidine-1-carbonyl)-4,4-dimethylpent-2-enenitrile to rapidly control dog PF suggests that adequate doses of a BTK inhibitor can replace corticosteroids not just in human PV but in other diseases where corticosteroids are used acutely.

What is claimed:

1. A method of treating pemphigus vulgaris or pemphigus foliaceus in a human in need thereof, said method comprising
administering to said human a therapeutically effective amount of a BTK inhibitor (R,E)-2-(3-(4-amino-3-(2-fluoro-4-phenoxyphenyl)-1H-pyrazolo[3,4-d]-pyrimidin-1-yl)piperidine-1-carbonyl)-4,4-dimethylpent-2-enenitrile.

2. The method of claim 1, wherein said BTK inhibitor is used in place of a corticosteroid therapy.

3. The method of claim 1, wherein said BTK inhibitor is used in combination with a corticosteroid therapy.

4. The method of claim 1, further comprising administering said BTK inhibitor in combination with a noncorticosteroidal immunosupressive and/or anti-inflammatory agent.

5. The method of claim 1, wherein said noncorticosteroidal immunosuppressive and/or anti-inflammatory agent is chosen from anti-CD20 antibody, anti-TNF antibody, anti-IL6 agent, anti-IL17 agent, and abatacept.

6. The method of claim 4, wherein said noncorticosteroidal immunosuppressive and/or anti-inflammatory agent is chosen from rituximab, tositumomab, veltuzumab, obinutuzumab, Enbrel, and ofatumumab, or a biosimilar version thereof.

7. A method of eliminating or reducing a therapeutic dose of a corticosteroid therapy used in the treatment of pemphigus vulgaris or pemphigus foliaceus in a human in need thereof, wherein said corticosteroid therapy is used as the first or second line in chronic maintenance therapy, said method comprising
administering to said human a therapeutically effective amount of a BTK inhibitor (R,E)-2-(3-(4-amino-3-(2-fluoro-4-phenoxyphenyl)-1H-pyrazolo[3,4-d]-pyrimidin-1-yl)piperidine-1-carbonyl)-4,4-dimethylpent-2-enenitrile.

8. The method of claim 7, wherein said BTK inhibitor is used in place of said corticosteroid therapy.

9. The method of claim 7, wherein said BTK inhibitor is used in combination with said corticosteroid therapy.

10. The method of claim 7, further comprising administering said BTK inhibitor in combination with a noncorticosteroidal immunosupressive and/or anti-inflammatory agent.

11. The method of claim 10, wherein said noncorticosteroidal immunosuppressive and/or anti-inflammatory agent is chosen from anti-CD20 antibody, anti-TNF antibody, anti-IL6 agent, anti-IL17 agent, and abatacept.

12. The method of claim 10, wherein said noncorticosteroidal immunosuppressive and/or anti-inflammatory agent is chosen from rituximab, tositumomab, veltuzumab, obinutuzumab, Enbrel, and ofatumumab, or a biosimilar version thereof.

13. A method of treating acute flares of pemphigus vulgaris or pemphigus foliaceous in a human in need thereof, wherein a corticosteroid therapy is used as the first or second line in chronic maintenance therapy, comprising
administering to said human a therapeutically effective amount of a BTK inhibitor (R,E)-2-(3-(4-amino-3-(2-fluoro-4-phenoxyphenyl)-1H-pyrazolo[3,4-d]-pyrimidin-1-yl)piperidine-1-carbonyl)-4,4-dimethylpent-2-enenitrile.

14. The method of claim 13, wherein said BTK inhibitor is used in place of said corticosteroid therapy.

15. The method of claim 13, wherein said BTK inhibitor is used in combination with said corticosteroid therapy.

16. The method of claim 13, further comprising administering said BTK inhibitor in combination with a noncorticosteroidal immunosupressive and/or anti-inflammatory agent.

17. The method of claim 16, wherein said noncorticosteroidal immunosuppressive and/or anti-inflammatory agent is chosen from anti-CD20 antibody, anti-TNF antibody, anti-IL6 agent, anti-IL17 agent, and abatacept.

18. The method of claim 16, wherein said noncorticosteroidal immunosuppressive and/or anti-inflammatory agent is chosen from rituximab, tositumomab, veltuzumab, obinutuzumab, Enbrel, and ofatumumab, or a biosimilar version thereof.

* * * * *